United States Patent
Issadore et al.

(10) Patent No.: US 11,786,914 B2
(45) Date of Patent: Oct. 17, 2023

(54) MAGNETIC SEPARATION FILTERS AND MICROFLUIDIC DEVICES USING MAGNETIC SEPARATION FILTERS

(71) Applicant: The Trustees of the University of Pennsylvania, Philadelphia, PA (US)

(72) Inventors: David Issadore, Philadelphia, PA (US); Venkata Yelleswarapu, Philadelphia, PA (US); Jina Ko, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1212 days.

(21) Appl. No.: 15/768,286

(22) PCT Filed: Oct. 4, 2016

(86) PCT No.: PCT/US2016/055308
§ 371 (c)(1),
(2) Date: Apr. 13, 2018

(87) PCT Pub. No.: WO2017/074658
PCT Pub. Date: May 4, 2017

(65) Prior Publication Data
US 2018/0297039 A1  Oct. 18, 2018

Related U.S. Application Data

(60) Provisional application No. 62/246,894, filed on Oct. 27, 2015.

(51) Int. Cl.
*B03C 1/28*  (2006.01)
*B03C 1/01*  (2006.01)
(Continued)

(52) U.S. Cl.
CPC ............... *B03C 1/288* (2013.01); *B03C 1/01* (2013.01); *B03C 1/032* (2013.01); *B03C 1/034* (2013.01);
(Continued)

(58) Field of Classification Search
None
See application file for complete search history.

(56) References Cited

U.S. PATENT DOCUMENTS

| 4,279,748 A | 7/1981 | Inoue |
| 2003/0134316 A1* | 7/2003 | Tashiro ............... B01F 13/0809 435/6.11 |

(Continued)

FOREIGN PATENT DOCUMENTS

| JP | 07130528 A | 5/1995 |
| WO | 2015013364 A1 | 1/2015 |

OTHER PUBLICATIONS

Earhart et al., Microfabricated Magnetic Sifter for High-throughput and High-gradient Magnetic Separation, J. Magn. Mater., May 2009, 321:(10)—pp. 1436-1439.

(Continued)

*Primary Examiner* — Lyle Alexander
*Assistant Examiner* — Bryan Kilpatrick
(74) *Attorney, Agent, or Firm* — BakerHostetler

(57) ABSTRACT

A magnetic separation filter has an unsupported magnetically soft material layer having a plurality of pores, and, optionally, a passivation layer disposed on the magnetically soft material layer. The magnetic separation filter may be part of a microfluidic device having a lateral flow channel and a vertical flow magnetic separation filter. The magnetic separation device may be used to separate magnetically tagged particles, such as cells.

16 Claims, 38 Drawing Sheets

(51) Int. Cl.
*G01N 33/574* (2006.01)
*B03C 1/032* (2006.01)
*B03C 1/034* (2006.01)
*G01N 33/543* (2006.01)

(52) U.S. Cl.
CPC ... *G01N 33/5434* (2013.01); *G01N 33/54333* (2013.01); *G01N 33/574* (2013.01); *B01L 2300/0681* (2013.01); *B03C 2201/18* (2013.01); *B03C 2201/26* (2013.01)

(56) References Cited

U.S. PATENT DOCUMENTS

| | | | |
|---|---|---|---|
| 2004/0028875 A1 | 2/2004 | Van Rijn et al. | |
| 2005/0148064 A1 | 7/2005 | Yamakawa et al. | |
| 2007/0178603 A1* | 8/2007 | Takii | B01F 33/30 |
| | | | 436/174 |

OTHER PUBLICATIONS

International Preliminary Report on Patentability for International Application No. PCT/US2016/055308, dated May 1, 2018—7 pages.
International Search Report and Written Opinion for International Application No. PCT/US2016/055308, dated Dec. 8, 2016—7 pages.

* cited by examiner

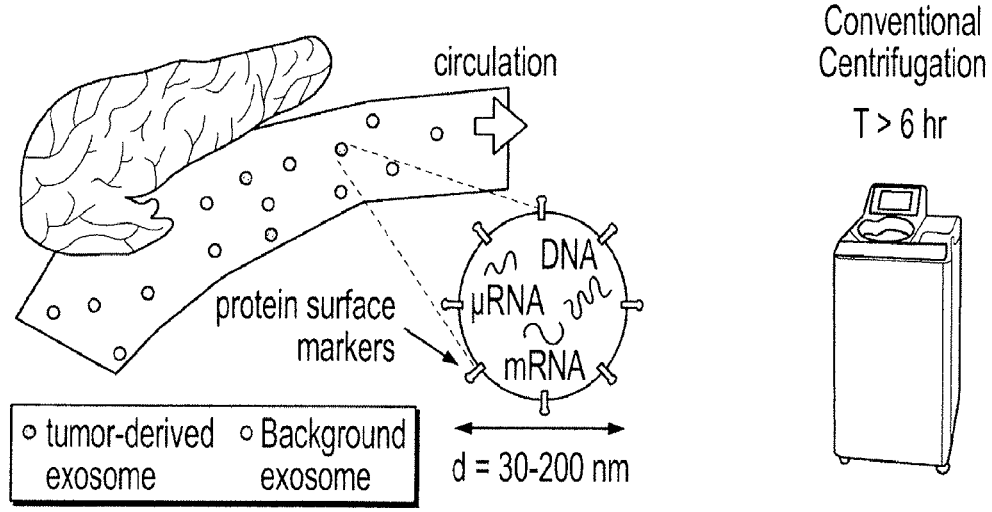
FIG. 20a
FIG. 20b
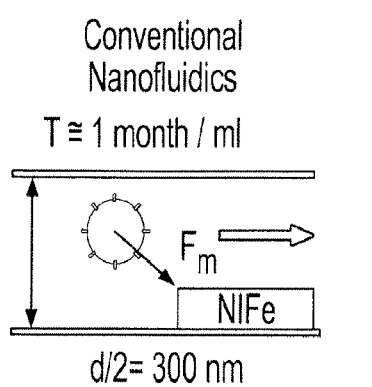
FIG. 20c
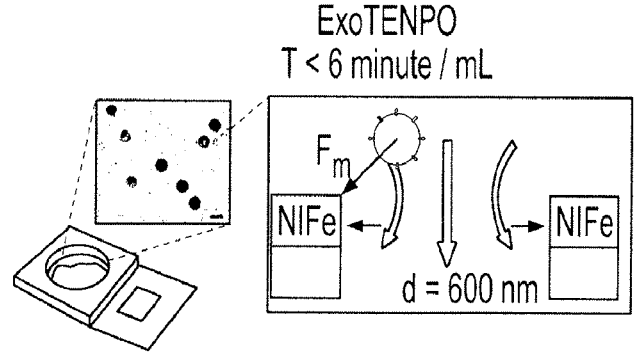
FIG. 20d
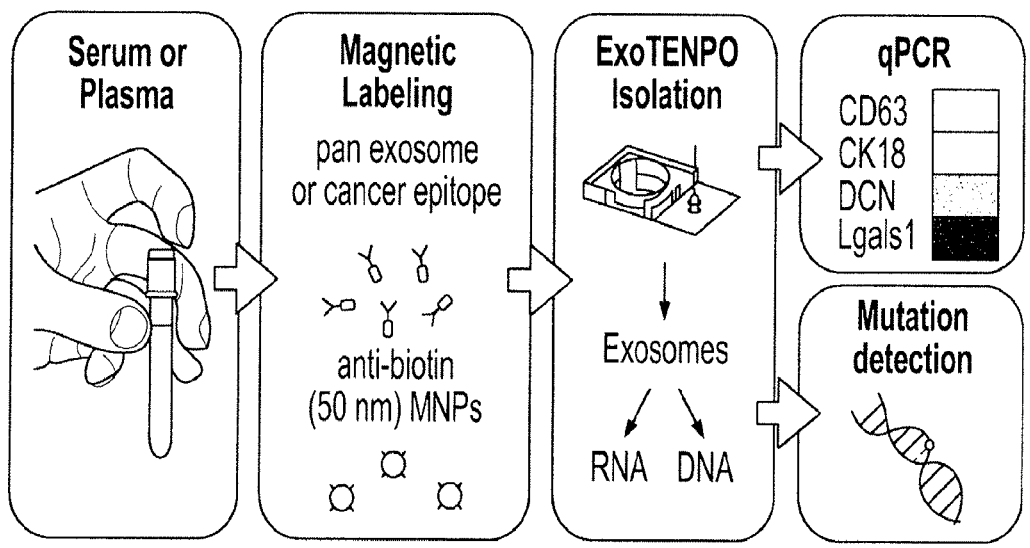
FIG. 20e

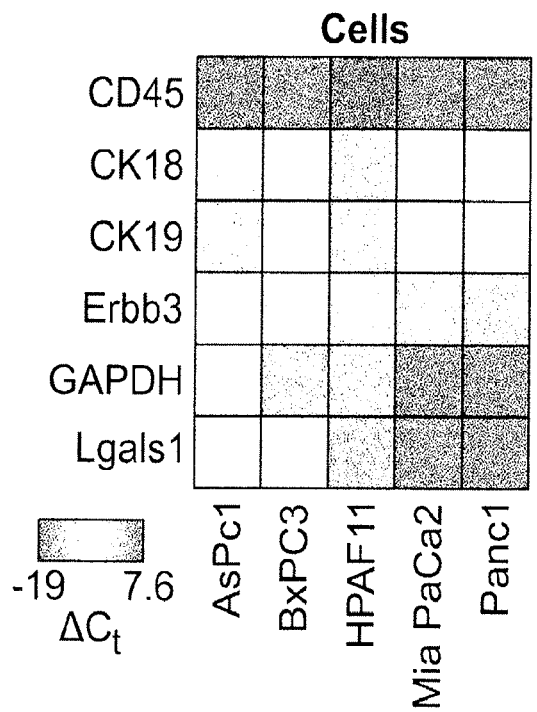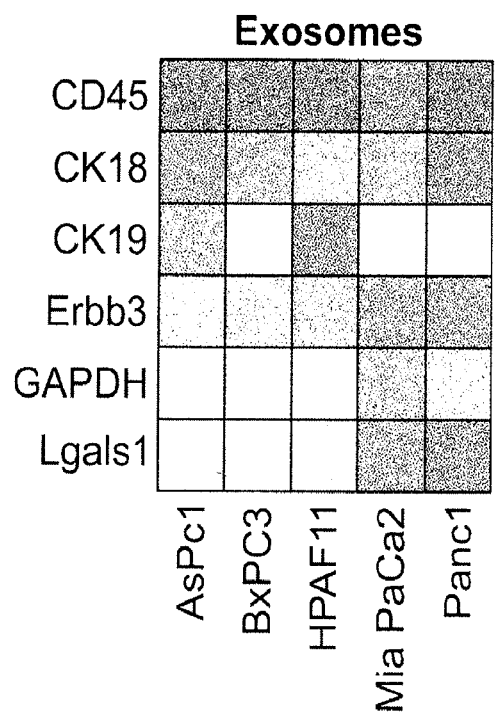
FIG. 23a  FIG. 23b
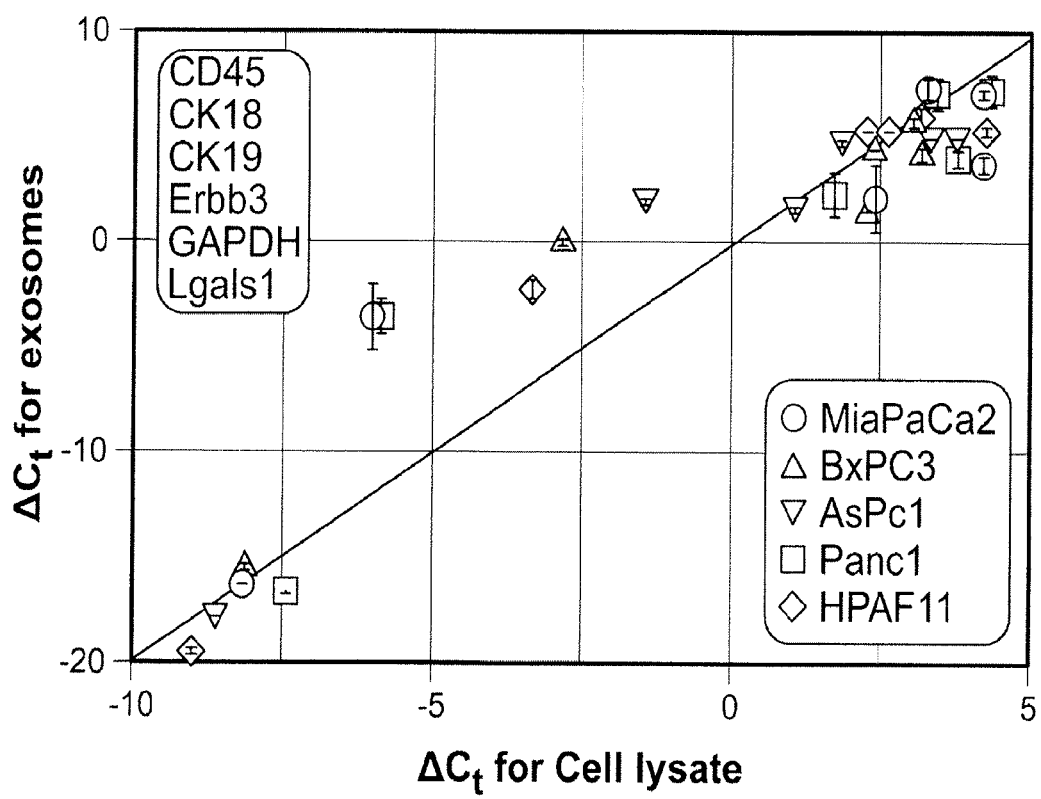
FIG. 23c

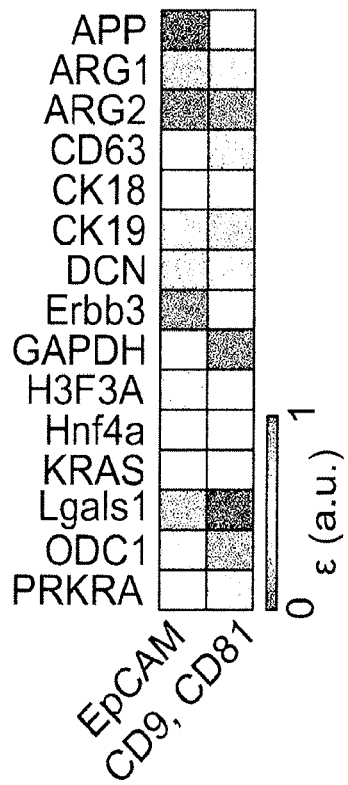
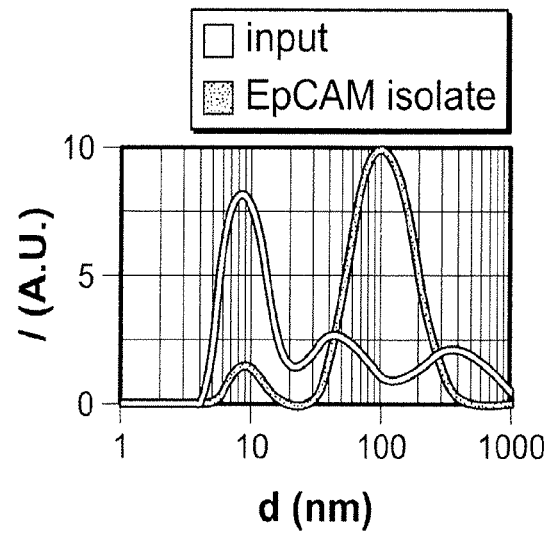
FIG. 24a
FIG. 24b
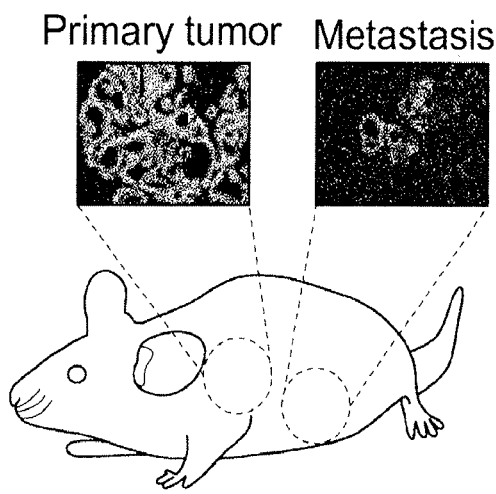
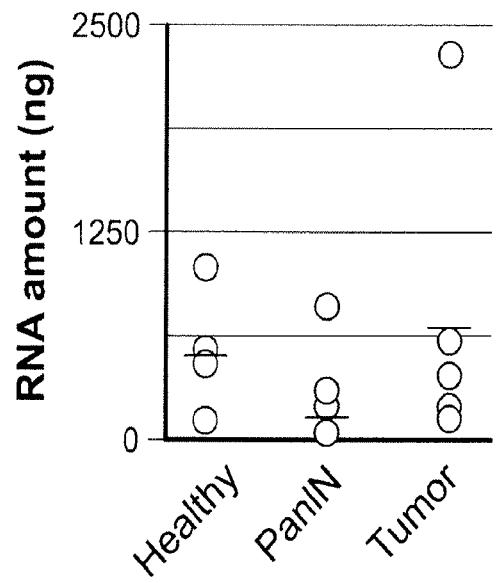
FIG. 24c
FIG. 24d

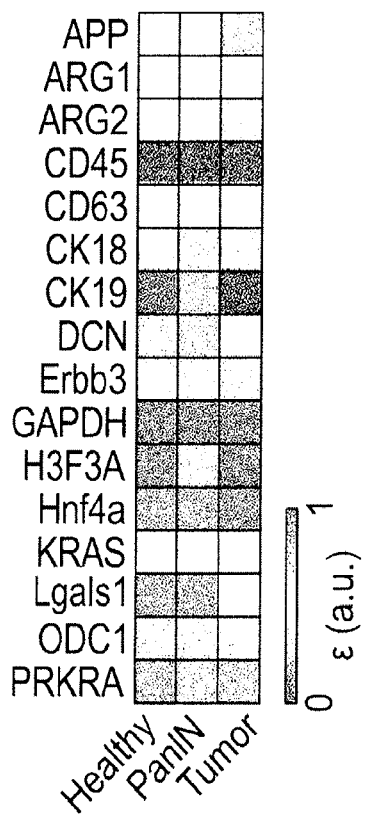
FIG. 24e
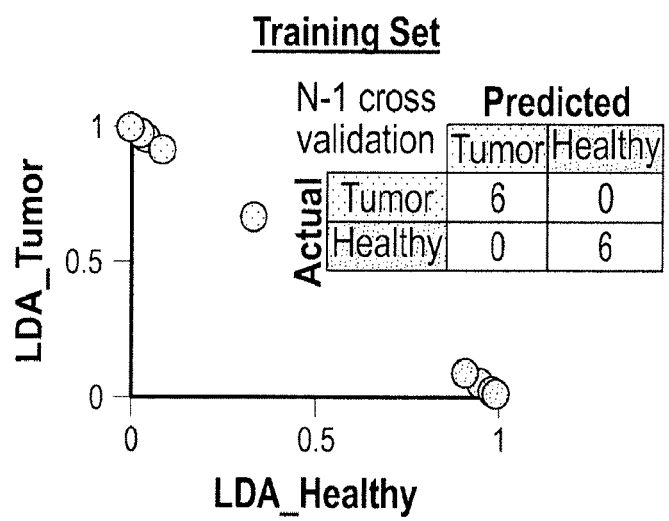
FIG. 24f
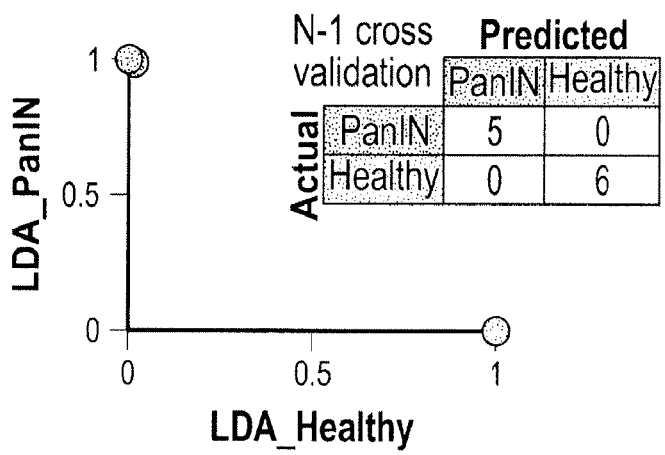
FIG. 24g
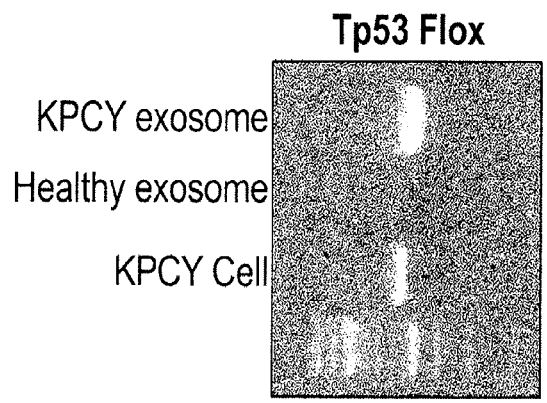
FIG. 24h
FIG. 24i

Training Set

N-1 Cross Validation

Independent Test Set

Overall Results for sample 2 : <u>exosome rna kit</u>

RNA Area: 332.4  RNA Integrity Number (RN)  26 (8.02.04)
RNA Concentration: 723****  Result Flagging Color

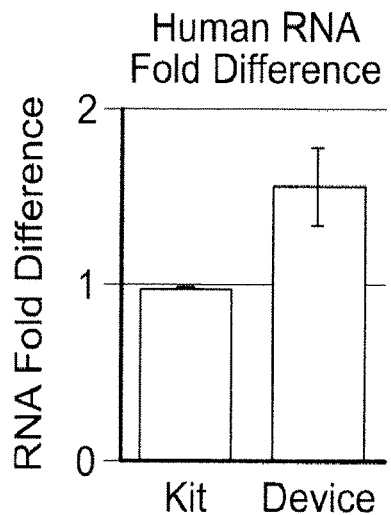

FIG. 29

```
% N-1 cross validation of the training set
status=[zeros(size(healthy(1,:)'));ones(size(sick(1,:)'))*1];
% labeling each group (healthy = 0, sick = 1)
obj = ClassificationDiscriminant.fit([healthy';sick'],
status,'leaveout','on');
% Linear discriminant analysis with N-1 cross validation
label=kfoldPredict(obj)
% Predicted labels are generated for each sample
a=confusionmat(status,label)
% Confusion matrix is created using the actual label (status)
and the predicted label (label)

% Using the training set to test out the samples in the set
status=[zeros(size(healthy(1,:)'));ones(size(sick(1,:)'))*1];
% labeling each group (healthy = 0, sick = 1)
obj = ClassificationDiscriminant.fit([healthy';sick],status);
% Linear discriminant analysis
[label, score] = predict(obj,test');
% Predicted labels and scores are generated for each
sample in the test set
```

FIG. 30

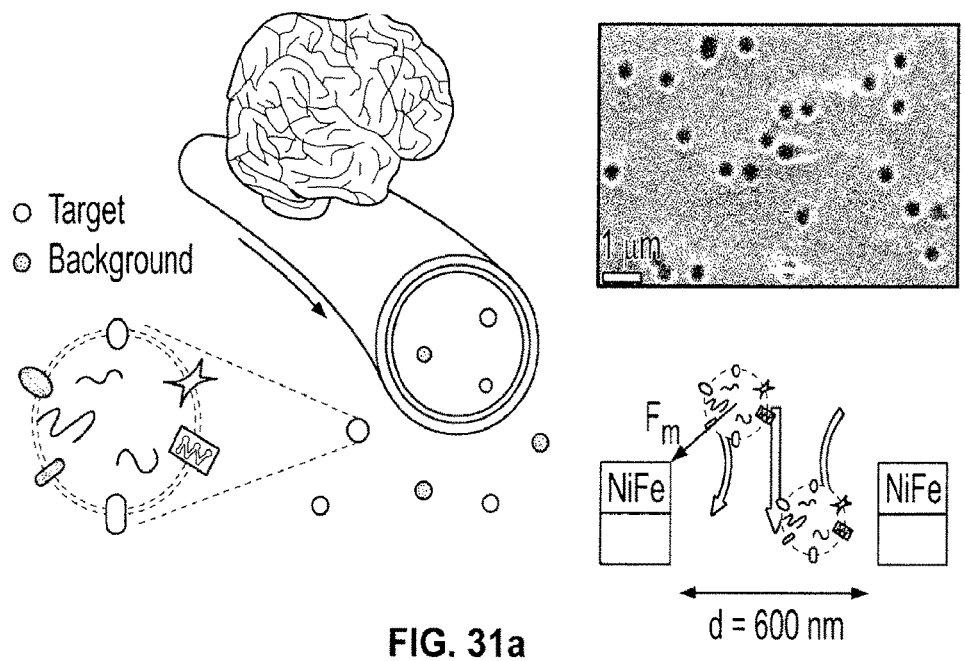
FIG. 31a
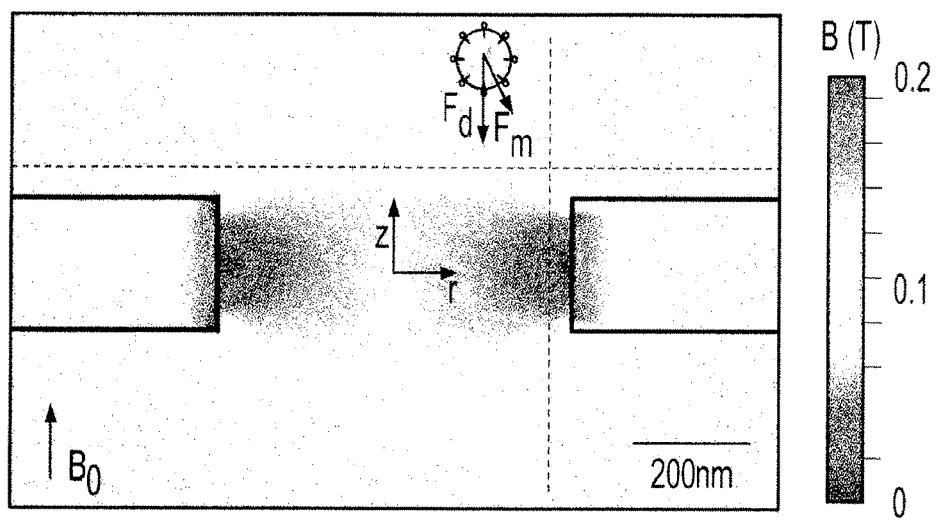
FIG. 31b
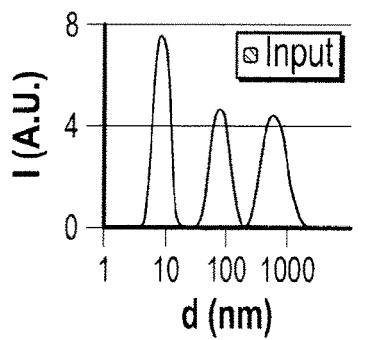
FIG. 31c
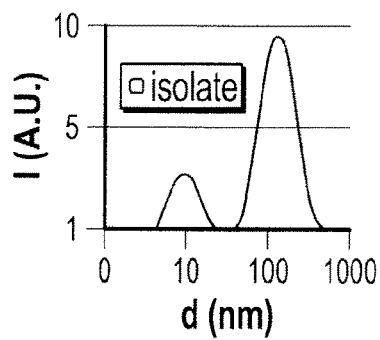 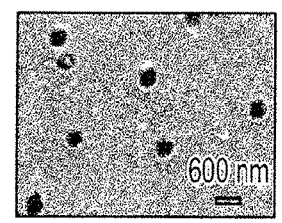
FIG. 31d

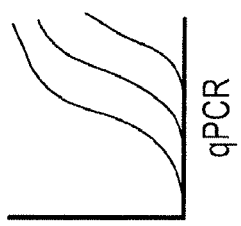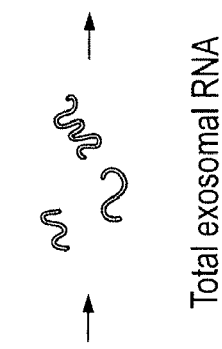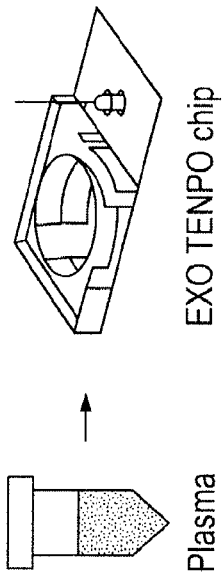
FIG. 31e

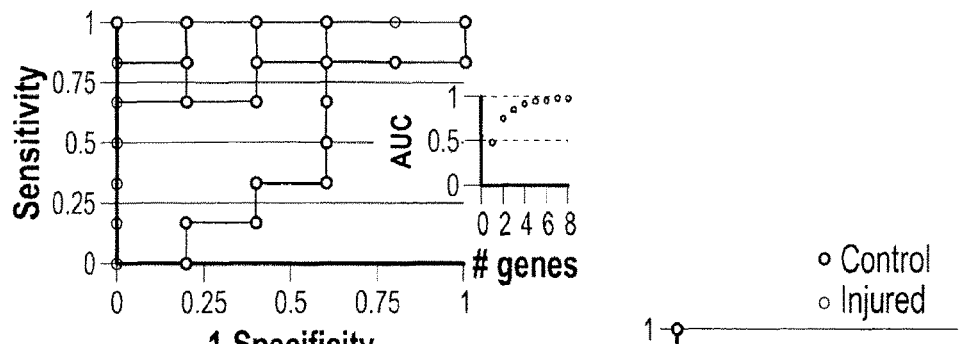
FIG. 34a
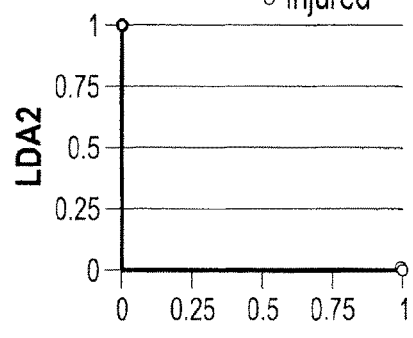
FIG. 34b
| Training set | | Predicted | |
|---|---|---|---|
| | | Control | Injured |
| Actual class | Control | 5 | 0 |
| | Injured | 0 | 5 |
FIG. 34c
| Test set | | Predicted | |
|---|---|---|---|
| | | Control | Injured |
| Actual class | Control | 5 | 0 |
| | Injured | 0 | 6 |
FIG. 34d

MAGNETIC SEPARATION FILTERS AND MICROFLUIDIC DEVICES USING MAGNETIC SEPARATION FILTERS

CROSS REFERENCE TO RELATED APPLICATIONS

This application is the U.S. National Phase application of PCT International Application PCT/US2016/055308, filed on Oct. 4, 2016, which claims the benefit of U.S. Provisional Application No. 62/246,894, titled MAGNETIC SEPARATION FILERS AND MICROFLUIDIC DEVICES USING MAGNETIC SEPARATION FILERS, filed on Oct. 27, 2015, the entirety of which applications are is incorporated by reference herein.

FIELD OF THE INVENTION

The present invention relates to magnetic separation devices to selectively and rapidly sort objects. The present invention also relates to microfluidic devices comprising magnetic separation devices and methods for separating magnetically tagged objects.

BACKGROUND INFORMATION

The isolation of rare biological targets, such as circulating tumor cells (CTCs), pathogenic bacteria, circulating microvesicles (CµVs), or exosomes, from easily accessible biological fluids is of great importance for disease monitoring and diagnostics. Detection platforms that utilize micro- and nanoscale structures, where dimensions can be designed to match those of the biological target, have been utilized for highly efficient and selective sorting.

One method that has been particularly successful for isolating rare cells from clinical samples is magnetophoresis, in which immunomagnetically labeled targets are isolated from suspensions using strong and highly localized magnetic forces. Due to the lack of magnetic susceptibility of biological materials, magnetic sorting can be performed directly on unprocessed clinical samples (e.g., blood) and environmental samples (e.g., drinking water). Furthermore, strong forces can be applied without the need for a power supply or moving parts, making these devices well suited for use in practical settings outside of the laboratory.

Much work has been done to develop and improve magnetic isolation using microfabrication techniques. Micropatterned magnetic field profiles have been engineered using lithographically defined current carrying wires and paramagnetic materials. Additionally, a number of bottom-up fabrication strategies have been developed to create strong magnetic forces. Microfluidic channels have been used in conjunction with patterned magnetic fields to bring targeted cells close to the high magnetic field gradients, to provide predictable flow velocities, and to minimize non-magnetic retention.

Earhart et al. (J Magn Mater, May 2009; 231(10): 1436-1439; doi:10.1016/j.jmmm.2009.02.062) disclose a vertical flow micro-magnetic sorting device comprising a silicon nitride sifter formed on a silicon wafer. The sifter is micropatterned with rectangular slots and coated with a cobalt tantalum zirconium (CoTaZr) film, which is rendered hydrophilic with a silicon dioxide ($SiO_2$) coating. The sorting device is formed using advanced semiconductor processing techniques, including photolithography and etching. Fluid flows vertically through the rectangular slots of the silicon nitride micropores coated with the magnetic CoTaZr film, and magnetically labeled particles are captured in the slots.

In the last decades an enormous amount has been learnt about the molecular changes in tumors and surrounding tissue associated with the formation of cancer, even at its earliest stages. However, because many tumors such as brain, pancreatic, and lung are located in regions of the body that are difficult to surgically access, and for which repeat biopsy is often impossible, use of these molecular changes to diagnose or to guide the treatment of cancer has been limited. The development of new technologies to measure the sparse tumor materials present in patient blood samples to minimally-invasively monitor the molecular state of cancer in real time have generated enormous enthusiasm. In recent years, nanoscale exosomes (30 nm-200 nm diameter), which originate from tumor cells and can be found circulating in the blood (FIG. 20a) have been discovered to contain molecular information relevant for disease diagnostics, disease monitoring, and drug efficacy screening. Despite their enormous potential, it has proven challenging to use conventional technology to establish the clinical utility of exosome biomarkers and to use these biomarkers to improve patient care. Due to their small sizes (30 nm-200 nm), conventional size-based isolation of exosomes is time consuming (>6 hr), results in co-purification of cell debris, and cannot selectively isolate specific sub-populations of exosomes or differentiate exosomes from other extracellular vesicles (e.g. microvesicles, oncosomes) (FIG. 20b).

While microfluidic technology has demonstrated enormous success in precisely sorting and detecting rare cells, the scaling of these approaches to the nanoscale has been limited by the inherently low throughput and susceptibility to clogging of nanoscale fluid channels (FIG. 20c). To illustrate this point, when the dimensions of a microfluidic chip designed to sort cells is reduced in scale by 100× to sort exosomes, the processing time increases by 10,000×, resulting in runtimes T>1 year for clinically relevant sample volumes V~10 mL.

There is a need for magnetic separation devices that have improved sorting efficiencies and/or greater throughput, which can be produced inexpensively and incorporated into microfluidic devices.

SUMMARY OF THE INVENTION

The present invention relates to magnetic separation devices, microfluidic/nanofluidic devices comprising magnetic separation devices, methods of making the magnetic separation devices, and methods of trapping particles using the magnetic separation devices.

Aspect 1. A magnetic separation device comprising:
a layer of magnetically soft material having a plurality of pores;
optionally, a passivation layer adjacent said layer of magnetically soft material.

Aspect 2. The device according to Aspect 1, wherein the layer of magnetically soft material is formed on a membrane comprising a plurality of pores.

Aspect 3. The device according to Aspect 2, wherein the membrane comprises a material chosen from cellulose, polymers and metal oxides.

Aspect 4. The device according to Aspect 2, wherein the membrane comprises a material chosen from polycarbonate, polyester, nylon, and aluminum oxide.

Aspect 5. The device according to Aspect 2, wherein the layer of magnetically soft material has a thickness ranging from about 50 nm to about 1 µm.

Aspect 6. The device according to Aspect 1, wherein the layer of magnetically soft material is unsupported.

Aspect 7. The device according to Aspect 6, wherein the layer of magnetically soft material has a thickness ranging from about 3 µm to about 50 µm.

Aspect 8. The device according to Aspect 1, wherein the pores have an average diameter ranging from about 100 nm to 200 µm.

Aspect 9. The device according to Aspect 1, wherein the pores have an average diameter ranging from about 500 nm to about 50 µm.

Aspect 10. The device according to Aspect 1, wherein the magnetically soft material is a nickel-iron alloy.

Aspect 11. The device according to Aspect 1, wherein the passivation layer comprises a material chosen from nickel and gold.

Aspect 12. The device according to Aspect 1, wherein the membrane comprises at least 1000 pores/mm$^2$.

Aspect 13. The device according to Aspect 1, wherein the pores have a shape selected from circular, oval, square, and rectangular.

Aspect 14. A microfluidic device comprising:
  at least one lateral flow channel; and
  at least one vertical flow magnetic separation filter in fluidic communication with the at least one lateral flow channel;
  wherein the at least one vertical flow magnetic separation filter comprises a layer of magnetically soft material, and, optionally, a passivation layer disposed on said layer of magnetically soft material.

Aspect 15. The microfluidic device of Aspect 14, further comprising a flow converter positioned between the at least one lateral flow channel and the at least one vertical flow magnetic separation filter.

Aspect 16. The microfluidic device of Aspect 15, wherein the flow converter comprises a plurality of branching passages capable of evenly distributing fluid to the at least one vertical flow magnetic separation filter.

Aspect 17. The microfluidic device of Aspect 14, wherein the device comprises n vertical flow magnetic separation filters, wherein n=2 to 10.

Aspect 18. The microfluidic device of Aspect 14, wherein the at least one vertical flow magnetic separation filter has a surface area of at least 0.2 cm$^2$.

Aspect 19. The microfluidic device according to Aspect 14, wherein the magnetically soft material is formed on a membrane comprising a plurality of pores.

Aspect 20. The microfluidic device according to Aspect 19, wherein the membrane comprises a material chosen from polycarbonate, polyester, nylon, and aluminum oxide.

Aspect 21. The microfluidic device according to Aspect 14, wherein the magnetically soft material is unsupported.

Aspect 22. The microfluidic device according to Aspect 14, wherein the pores have an average diameter ranging from about 100 nm to 100 µm.

Aspect 23. The microfluidic device according to Aspect 14, wherein the magnetically soft material is a nickel-iron alloy.

Aspect 24. The microfluidic device according to Aspect 14, wherein the magnetic separation filter comprises at least 1000 pores/mm$^2$.

Aspect 25. The microfluidic device according to Aspect 14, wherein the pores have a shape selected from circular, oval, square, and rectangular.

Aspect 26. A method of making a magnetic separation filter comprising electroforming a layer of a magnetically soft material on a mold, wherein the mold comprises pillars or protrusions corresponding to pores in the layer of magnetically soft material, and removing the layer of magnetically soft material from the mold, and, optionally, forming a passivation layer on the layer of magnetically soft material.

Aspect 27. The method according to Aspect 26, wherein removing the layer of magnetically soft material from the mold comprises mechanically removing the layer of magnetically soft material from the mold.

Aspect 28. A method for separating magnetically tagged particles in a microfluidic device, comprising:
  exposing a vertical flow magnetic separation filter to an external magnetic field, wherein the vertical flow magnetic separation filter comprises a layer of magnetically soft material comprising a plurality of pores, and, optionally, a passivation layer disposed on the layer of magnetically soft material;
  flowing a suspension comprising the magnetically tagged particles through a lateral flow channel in a microfluidic device;
  capturing the magnetically tagged particles in the vertical flow magnetic separation filter;
  removing the external magnetic field; and
  releasing the captured magnetically tagged particles.

Aspect 29. The method according to Aspect 28, wherein the magnetically tagged particles are selected from cells, exosomes, molecules, nucleic acids, and polypeptides.

Aspect 30. The method according to Aspect 29, wherein the magnetically tagged particles are selected from exosomes.

Aspect 31. The method according to Aspect 28, wherein flowing a suspension comprising the magnetically tagged particles is performed at a flow rate of at least 10 ml/h.

Aspect 32. The method according to Aspect 28, wherein the vertical flow magnetic separation filter comprises a plurality of vertical flow magnetic separation filters.

Aspect 33. The method according to Aspect 30, further comprising extracting the nucleic acids from the exosomes.

Aspect 34. The method according to Aspect 33, further comprising analyzing the nucleic acids using qPCR.

Aspect 35. A method of diagnosing a condition in a subject comprising:
  obtaining a fluid sample from the subject;
  magnetically labeling exosomes in the plasma sample with biotinylated antibodies and anti-biotin magnetic nanoparticles;
  exposing a magnetic separation filter to an external magnetic field, wherein the magnetic separation filter comprises a layer of magnetically soft material comprising a plurality of pores;
  flowing a suspension comprising the magnetically labeled exosomes through the magnetic separation filter to capture the magnetically labeled exosomes;
  removing the external magnetic field to release the capture magnetically labeled exosomes;
  extracting nucleic acids from the magnetically labeled exosomes; and
  analyzing the nucleic acids to determine whether the subject has the condition.

Aspect 36. The method according to Aspect 35, wherein the condition is selected from cancer or brain injury.

Aspect 37. The method according to Aspect 36, wherein the condition is pancreatic or prostate cancer.

Aspect 38. The method according to Aspect 35, wherein the fluid sample is a blood sample or urine sample.

Aspect 38. The method according to Aspect 35, wherein the nucleic acids are analyzed using qPCR.

BRIEF DESCRIPTION OF THE DRAWINGS

FIG. 20a shows the circulation of nanoscale exosomes which are shed by tumor cells and circulate amongst a vast, complex background of non-tumor derived material.

FIG. 20b. shows a conventional ultracentrifugation method that isolates exosomes based on size and takes more than 6 hrs.

FIG. 20c shows a schematic of a conventional nanofluidic device, sized appropriately to isolate exosomes.

FIG. 20d shows a schematic of an Exosome sorting Track Etched magnetic NanoPOre (ExoTENPO) chip in accordance with an embodiment of the present disclosure, which recapitulates the advantages of the nanofluidic approach but can operate at >100× flow rates and is robust against clogging.

FIG. 20e shows a schematic of the process using a chip-based assay beginning with serum or plasma, magnetically labeled exosomes are isolated using ExoTENPO, and their cargos (RNA, DNA) are isolated on-chip for downstream molecular analyses.

FIG. 23a shows the exosomal RNA expression of six human cell lines and six genes.

FIG. 23b shows cellular RNA expression of six human cell lines and six genes. In the heat map, data is normalized to the mean Ct values of all genes.

FIG. 23c shows a scatter plot of exosomal RNA expression level and cellular RNA expression level to measure correlation between expression in cell lysate and in the exosomes. Genes are color coded and cell lines are coded by shape. Error bars are standard deviation from replicate measurements.

FIG. 24a shows a heat map using two different capture markers (EpCAM, Pan—CD9, CD81) to show the expression level differences of 15 exosomal mRNAs from healthy mouse plasma and healthy mouse plasma spiked with mouse pancreatic cancer cell cultured media (PD7591).

FIG. 24b shows dynamic light scattering (DLS) measurement of the input (PD7591 cultured media) and the isolate from a chip with EpCAM capture according to one embodiment.

FIG. 24c shows a murine model for pancreatic cancer. The KPCY mouse is a genetically engineered mouse model for pancreatic cancer, modified to include a fluorescent (YFP) lineage tracer.

FIG. 24d shows total that RNA amount (ng) per mouse for three different groups (healthy, PanIN, and tumor) did not show statistically significant difference.

FIG. 24e shows a heat map of 15 different gene expression levels from three different groups (healthy, PanIN, and tumor).

FIGS. 24f and 24G shows linear discriminant analysis (LDA) vectors algorithmically generated based on the RNA expression levels to separate healthy mice (green), precancerous mice PanIN (blue), and cancer mice (red).

FIG. 24h shows a confusion matrix demonstrating the ability of the method according to one embodiment to identify healthy versus PanIN versus using N−1 cross-validation.

FIG. 24i shows the analysis of exosomal DNA using the KPCY mouse model according to one embodiment. Western blot for Tp53 Flox for KPCY mouse exosome vs. healthy mouse exosome. KPCY mouse cell was used as a positive control.

FIG. 29 shows the recovery of exosomal RNA using an ExoTENPO device according to one embodiment in human plasma samples compared to the conventional (kit) method (Total exosome isolation kit, Life Technologies).

FIG. 30 shows the MATLAB codes for the linear discriminant analysis (LDA). Built-in LDA function is used to test the training set using N−1 cross validation and to test the samples in the test using the validated training set.

FIG. 31A shows a schematic diagram of the capture of exosomes secreted after a traumatic brain injury.

FIG. 31B shows a finite element simulation of a magnetic field plot and capture of an brain-derived exosome.

FIG. 31C shows the separation and isolation of brain-derived exosomes.

FIG. 31D shows a scanning electron micrograph of brain-derived exosomes trapped on an ExoTENPO device according to one embodiment.

FIG. 31E shows the process for preparing and analyzing a sample for detecting traumatic brain injury according to one embodiment.

FIG. 34A shows the sensitivity and specificity of diagnosis of mTBI mice.

FIG. 34B shows LDA analysis of the control group and injured group.

FIGS. 34C and 34D show confusion matrices for a training set and test set.

DETAILED DESCRIPTION OF THE INVENTION

One aspect of the present invention relates to a magnetic separation device. As used herein, the phrase "magnetic separation device" is used to refer to a device through which material flows through a magnetic separation filter, and which magnetically captures targeted objects. The targeted objects may be magnetically tagged objects, such as, for example, cells, molecules, nucleic acids, proteins, etc.

In at least one embodiment, a magnetic separation filter comprises a magnetically soft material comprising a plurality of holes through which material may pass. When a magnetic field is applied to the magnetic separation filter, magnetically tagged objects may be captured as they pass through the pores of the magnetic separation filter.

As used herein, the terms "pore" and "micropore" are used interchangeably to refer to channels that pass completely through the magnetic separation filter, i.e., continuous channels that pass from one surface of the filter to the opposite surface of the filter.

Figure 1A:
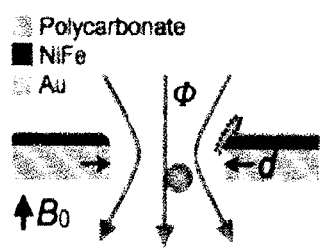
FIG. 1a is a schematic representation of a pore within a magnetic separation device according to an embodiment of the present invention.
Figure 1B:
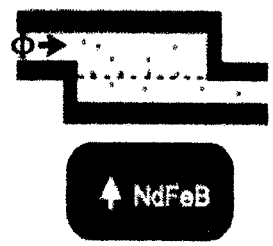
FIG. 1b is a schematic representation of a microfluidic device comprising a vertical flow magnetic separation filter according to an embodiment of the present invention.
Figure 1C:
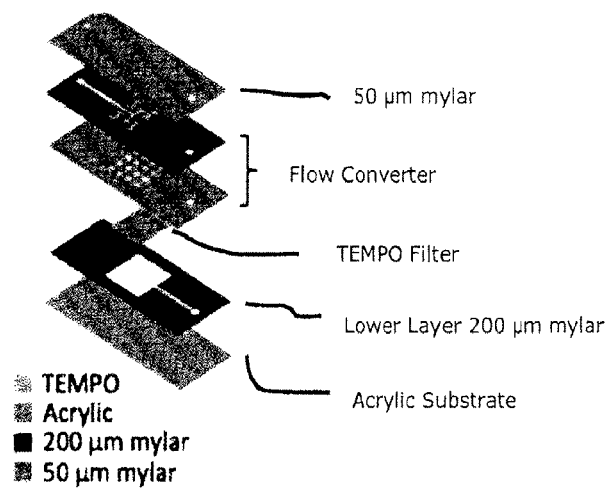
FIG. 1c is an exploded view of a microfluidic device comprising a vertical flow magnetic separation filter according to an embodiment of the present invention.
Figure 1D:
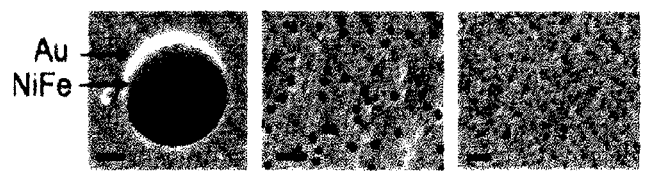
FIG. 1d is a series of SEM micrographs of a magnetic separation device at different magnifications according to an embodiment of the present invention.

FIG. 1d shows SEM micrographs of the pores of a magnetic separation filter, according to an embodiment of the present invention, with scale bars (from left to right) of 2 μm, 25 μm, and 200 μm.

The layer of magnetically soft material in the magnetic separation device may comprise a material selected based on its magnetic properties.

As used herein, the phrase "magnetically soft material" refers to a material which can become magnetized by a relatively low-strength, external magnetic field, e.g., by a magnet placed in close proximity to the material, that returns to a state of relatively low residual magnetism when the external magnetic field is removed.

In at least one embodiment, the magnetically soft material is capable of having an induced magnetic field when an external magnetic field is applied. The magnetically soft material may also be selected based on the magnetic remanence, i.e., the materials ability to return to a non-magnetic state when the external magnetic field is removed.

In at least one embodiment, the magnetically soft material is selected from permalloys, which include allows of nickel and iron. In accordance with at least one embodiment, the magnetically soft material is $Ni_{20}Fe_{80}$, an alloy which comprises 20% nickel and 80% iron.

The magnetic separation filter may comprise a passivation layer to protect the magnetically soft material from undesired interaction or reaction with fluids that the magnetic separation filter may come in contact with. For example, the passivation layer may protect the magnetically soft material from oxidation. In at least one embodiment, the passivation layer is comprised of a material chosen from inert materials, such as, for example, gold or nickel. Other materials known to those skilled in the art capable of protecting the magnetically soft material from oxidation may be used.

According to at least one embodiment, the magnetic separation filter comprises a membrane having a plurality of pores, a layer comprising a magnetically soft material, and a passivation layer.

The magnetically soft material and the passivation layer, if present, may be formed on the membrane using any technique known in the art. For example, the materials may be deposited by thermal evaporation, sputtering, chemical vapor deposition, electroplating, etc.

In at least one embodiment, the membrane is a material chosen from cellulosic, polymers, and metal oxide films. Examples of materials that may be used include, but are not limited to, paper, polycarbonate, polyester, nylon, and aluminum oxide. In at least one embodiment, the membrane is polycarbonate.

According to at least one embodiment, the membrane is composed of a material capable of being ion track etched. Ion track-etching can be used to provide uniform pore sizes in the membrane material. Pores formed by ion track-etching are generally circular in shape and are typically randomly arranged in the film. A magnetic separation filter comprising ion track-etched pores greater than 1 μm in diameter is referred to herein as a Track-Etched magnetic Micro-POre (TEMPO) filter, which are used in various embodiments and examples used throughout the present disclosure. Similarly, nanoscale magnetic separation filters comprising ion track-etched pores less than 1 µm in diameter are referred to as a Track-Etched magnetic Nano-POre (TENPO) filter. TEMPO and TENPO filters differ only in the size of the pores, and, unless specifically stated, the description of TEMPO filters herein can be equally applied to TENPO filters. Likewise, the terms "microfluidic" and "nanofluidic," as used herein, differ only in scale and all references to microfluidic are applicable to nanofluidic devices, unless stated otherwise.

An example of a TEMPO filter is shown in FIG. 1b. Other methods of forming pores within membranes known in the art can also be used. The magnetic separation devices of the present invention, however, are not intended to be limited to ion track-etched devices and one skilled in the art will recognize that unless otherwise specified, embodiments which refer to TEMPO or TENPO filters may include membrane-based magnetic separation filters formed by other methods. In at least one embodiment, the membrane is ion track-etched polycarbonate.

In accordance with at least one embodiment, the magnetically soft material is formed on the membrane by thermal evaporation, sputtering, chemical vapor deposition. The layer of magnetically soft material formed on the membrane may have a thickness ranging from about 50 nm to about 1 µm, such as from about 50 nm to about 200 nm. In at least one embodiment, the layer of magnetically soft material is evaporated on the membrane to form a layer having a thickness of 200 nm. The thickness of the magnetically soft material formed on the membrane may be limited by the technique used to deposit the material. The thickness should be sufficient to generate a magnetic field strong enough to capture the desired particles.

In at least one embodiment, the membrane comprises a commercially available ion track-etched polycarbonate membrane. The membrane is coated with a thin layer of magnetically soft material (e.g., permalloy) and a passivation layer of gold.

Polycarbonate membranes can be track-etched with pore sizes ranging from 15 nm to 100 µm over large areas ($A>10$ cm$^2$) for little cost (<$0.05/cm$^2$). The membranes are flexible and can be integrated into laminate sheet microfluidics patterned with laser micromachining. Due to the large size of the membranes ($A>1$ cm$^2$), highly efficient isolation ($\xi>10^4$) can be achieved at extremely high flow rates ($\Phi>10$ mL/hr). Without wishing to be limited by theory, it is believed that there are three main elements of the magnetic separation filter which maximize the magnetic force $F_m$ and minimize the drag force $F_d$ on targeted particles or objects (e.g., cells or exosomes), and thus optimize the sorting efficiency of the filter.

Strong magnetic field with high field gradient ($B\uparrow$, $\nabla B\uparrow$). The magnetic force $F_m \sim (B\cdot\nabla)B$ can be maximized by increasing the strength of the applied field B and its spatial changes $\nabla B$. The magnetic separation filter generates strong fields (e.g., $|B|=0.2$ T or more) due to the external magnet and strong, highly localized magnetic field gradients due to the pore geometry (FIG. 2a), to create strong magnetic trapping forces.

Figure 21A:
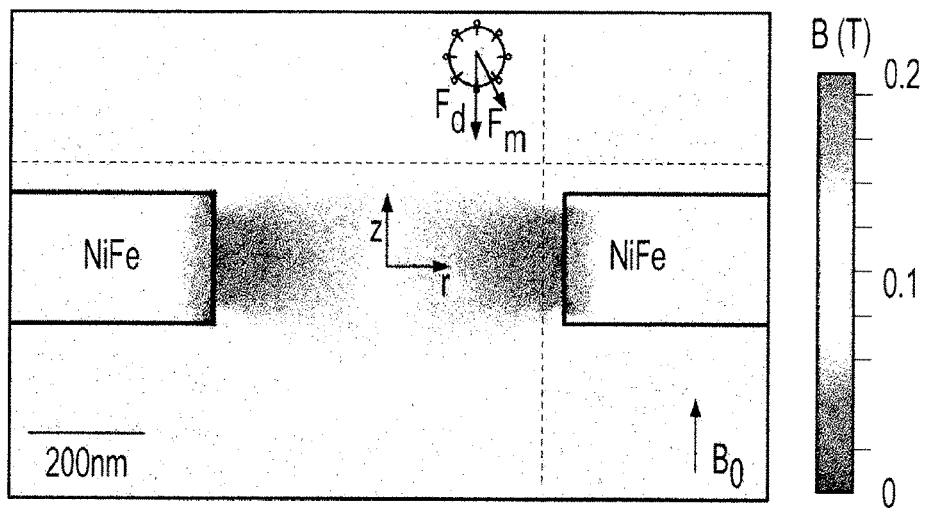
FIG. 21a shows the field strength |B| is plotted on the cross-section of a 600 nm ExoTENPO pore generated using finite element simulations

FIG. 21a shows an example of the magnetic fields in an Exosome sorting Track-Etched magnetic NanoPOre (Exo-TENPO) filter. In this example large fields $B\sim 0.4$ T are produced by the NdFeB magnet. Large field gradients $\nabla B$ are created by the NiFe coated nanopores (d=600 nm), which generate nanoscale field gradients at the pore's edge, where there is a transition from the highly magnetically susceptible NiFe ($\square\cong 10^5$) to water ($\square\cong -10^{-5}$). The close proximity of the exosomes to the regions of large magnetic force is controlled by the d=600 nm nanopores, which require each exosome to come within r=300 nm of the magnetic traps that are located at the pore's edge. Fundamentally, it is believed that these nanoscale traps can be created because there is no inherent length-scale in Maxwell's Equations for magnetostatics, in contrast to optical trapping where the size of a trap is limited by the wavelength of light.

Large flow channel area ($v\downarrow$). The hydrodynamic drag force $F_d=6\pi\mu aV$, where µ is the viscosity and v is the fluidic velocity, can be minimized by using columnar flow instead of low that is in-plane with a 1 in$^3$ NdFeB magnet (FIG. 1b). The cross sectional area of a vertical glow channel grows quadratically with the dimensions of the chip $L^2$, rather than linearly as with lateral flow. This feature may allow large flow rates $\Phi$ to be obtained, while keeping the flow velocity v small and the chip compact. Utilizing this approach, efficient sorting can be achieved at very high flow rates ($\Phi>10$ mL/hr). Close proximity of each particle (e.g., cells or exosomes) to the regions of strong magnetic force ($r\downarrow$). Because each particle must pass through a pore, each particle comes within r=d/2 of the edge of the pore, where d is the pore diameter and the pore has a circular cross-section. By choosing the pore size to be on the same size-scale as the object being trapped, it can be ensured that each particle comes within close proximity of the high-force trapping region.

In the example shown in FIG. 21a, to isolate an exosome, the magnetic trapping force $F_m$ must overcome the drag force $F_d$. The drag force is proportional to the flow velocity of the fluid $F_d \propto v$. In our design, the ExoTENPO chip consists of an $A_{dev}=15.2$ cm$^2$ sized membrane densely covered ($\rho>10^6$/cm$^2$) with magnetic nanopores. Thus, even at the high volumetric flow rates desired to process clinical samples $\phi>10$ mL/hr, the flow velocity v, and thus the drag force $F_d$, within each pore $v_z=\phi/(A_{dev}\rho A_{pore})$ can be kept small, where $A_{pore}$ is the cross sectional area of an individual pore.

A finite element model was developed to simulate the magnetic trapping capability of a TENPO according to the present disclosure using Matlab and Ansoft. Because each pore is axially symmetric in the example shown in FIG. 21a, the simulated magnetic field was calculated and plotted on the cross-section of the pore (FIG. 21a). The field strength B drops rapidly in distance from the edge of the nanopore, creating field gradients $\nabla B$ that lead to strong magnetic forces $F_m$. The nanopore was modeled as a disc, with a diameter d=600 nm and height h=200 nm, with boundary conditions of zero field at large distances. The magnetophoretic force $F_m$ on an exosome as it passes through a nanopore is calculated by combining the results from the simulation from with a simplified model for the exosome. The magnetic moment of the exosome is proportional to the number of magnetic nanoparticles (MNPs) n and the moment $m_p$ of the particle ($m=n*m_p$). The model assumes that the magnetic particles are fully magnetized by the externally applied field $B_o \approx 0.4$ T $\hat{z}$. It was assumed $m_s=9.27\times10^{-3}$ mA*µm$^2$ and that each targeted exosome has n>5 MNPs. The number of MNPs per exosome was calculated based on the limit imposed by steric hinderance on the smallest possible exosome, d=30 nm, assuming 50% maximum loading.

Figure 21B:
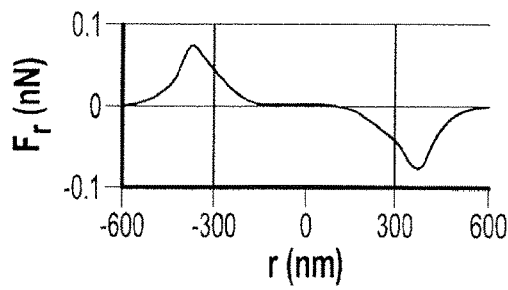
FIG. 21b shows the magnetophoretic force in the cylindrical direction $F_z$ is plotted along z, one exosome diameter d=100 nm from the edge of the pore.
Figure 21C:
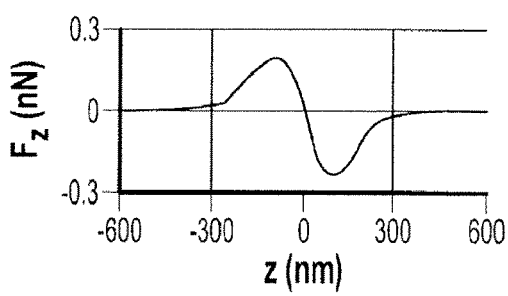
FIG. 21c shows the magnetophoretic force is plotted in the radial direction $F_r$ along r, one exosome diameter d=100 nm above the pore.

To interpret the finite element simulation, the process of capturing an exosome on ExoTENPO was separated into two steps. To be trapped, first an exosome is translated radially by magnetopheretic forces $F_r$ to the trap at the edge of the pore. The radial force $F_r$ drops off quickly in distance from the pore's edge (FIG. 21b). Therefore, in accordance with at least one embodiment, the pore diameter d is minimized to bring the target object (e.g., exosome) into close proximity to the regions where the field is the strongest. Once the exosome is translated to the pore's edge, then the magnetophoretic trapping force $F_z$=412 pN must overcome the drag force $F_d$ to successfully trap the exosome (FIG. 21c). The Stoke's drag on the trapped exosome F=6πμav is calculated, where μ is the viscosity of serum or plasma, and we find that even for extremely high flow rates (ϕ>>100 mL/hr) the magnetic force greatly exceeds the drag force $F_m$>>$F_d$. Thus, for the flow rates used in the example shown in FIG. 21a, the capture of an exosome is determined solely by its translation to the pore's edge, which is a function of its initial radial position r, the radial magnetophoretic force $F_r$, and its flow velocity $v_z$∝ϕ. From this analysis, the following observations were made: 1. The capture rate generally decreases as flow rate ϕ increases, 2. The capture rate generally increases as the pore's diameter d decreases, and 3. Because the probability of capturing an exosome is a function of its initial radial position in the pore, the capture rate can be increased by placing multiple filters in series, allowing the target object multiple, independent chances to be captured.

In accordance with another aspect of the present invention, the magnetic separation filter may comprise an unsupported layer of magnetically soft material.

As used herein, the term "unsupported layer of magnetically soft material" refers to a self-supporting layer of magnetically soft material, i.e., the layer of magnetically soft material does not need to be formed on another layer to provide support. The layer of magnetically soft material may have a thickness sufficient to provide the necessary strength to support itself within a magnetic separation device and to endure the pressure generated by flow through the device. The unsupported layer of magnetically soft material is not formed on a membrane.

In accordance with at least one embodiment, the unsupported layer of magnetically soft material is produced by electroforming the magnetically soft material. An electroformed nickel-iron alloy filter is referred to herein as a MAgnetic Nickel-iron Electroformed Trap (MagNET) filter. It is understood that methods and materials other than electroforming and nickel-iron alloys may be used to prepare magnetic separation filters comprising an unsupported layer of magnetically soft material. Therefore, embodiments which refer to MagNET filters may include magnetic separation filters having an unsupported layer of magnetically soft material formed by other methods In accordance with at least embodiment, the layer of magnetically soft material in a MagNET filter is formed by electroforming the layer on a mold. The mold may comprise any material on which the magnetically soft material may be electroformed and separated. For example, the layer of magnetically soft material may be electroformed and mechanically removed from the mold, such as by peeling the layer from the mold.

Alternatively, the layer of magnetically soft material may be removed by etching the mold away from the electroformed layer.

In accordance with at least one embodiment, the layer of magnetically soft material is electroformed on a mold and mechanically removed, enabling the mold to be reused to form additional layers.

According to at least one embodiment, the mold is made of copper. The mold may comprise a release layer to improve the release properties of the electroformed layer from the mold. A non-limiting example of a release layer formed on a copper mold is titanium.

The mold may comprise pillars or protrusions that correspond to the pores when the layer of magnetically soft material is electroformed on the mold. The pillars or protrusions may be made of the same or different material as the mold. In at least one embodiment, the pillars or protrusions are formed of a photoresist. The photoresist may be patterned using photolithography, for example. In at least one embodiment, the photoresist is a positive photoresist.

The sides of the pillars or protrusions may be tapered to improve release of the electroformed layer from the mold. Tapering the pillars or protrusions may prevent breaking the pillars or protrusions during removal and allow the reuse of the mold.

According to at least one embodiment, the degree of taper is selected based on the desired thickness of the electroformed layer, the shape of the pores, and/or the size of the size of the pores.

According to at least one embodiment, the layer of magnetically soft material in the MagNET filter has a thickness ranging from about 3 μm to about 40 μm, such as, for example from about 5 μm to about 25 μm. Thicker or thinner layers may also be used. The thickness may be limited by the manner in which the layer of magnetically soft material is formed. For example, a layer that is too thin may not be able to be removed from a mold, whereas a layer that is too thick may damage pillars or protrusions on the mold when it is removed. The thickness may also depend on the desired properties of the MagNET filter. Without wishing to be bound by theory, it is believed that MagNET can capture magnetic particles at the top and bottom of each pore.

The magnetically soft material in the MagNET filters may have a surface passivation layer, such as an inert material like gold or nickel.

In at least one embodiment, the pores of the MagNET filters may be selected from any desired shape. Because the molds can be made using techniques such as photolithography, there is no limit to the shape that may be created. For example, the pores may have circular, square, triangular, oval, or rectangular shapes. Other, more complex shapes are also possible. For example, the shape of the pore may be tailored to match the shape of the desired target particles. If the target particles are cell clusters, the pores may have a clover shape, for example, or another shape to maximize the potential for trapping the particles in the magnetic separation filter.

In at least one embodiment, the magnetic separation filter comprises pores at a pore density of at least 1000 pores/mm$^2$, such as, for example, at least 1500 pores/mm$^2$, at least 2000 pores/mm$^2$, or more.

In TEMPO/TENPO filters, due to the random nature of ion track-etching, increasing the pore density may increase the probability of pore overlap, which occur when one pore overlaps at least a portion of another pore. Pore overlap can increase the effective size of the overlapped pores, and thus negatively affect the ability of the TEMPO/TENPO filter to trap the target particles. Therefore, in at least one embodiment, the pore density may be selected to reduce the potential for overlap. In MagNET filters, pore density may be increased without overlap of the pores.

The pores may have an average diameter ranging from about 15 nm to about 100 μm, such as, for example, from about 100 nm to about 50 μm, from about 500 nm to about 50 μm, from about 500 nm to about 25 μm, or from about 500 nm to about 10 μm. In at least one embodiment, the pores have an average diameter less than about 50 μm, such as, for example, less than about 25 µm, less than 10 µm, less than about 5 µm, less than about 2 µm, or less than about 1 µm. As one skilled in the art would recognize, the size of the pores may be selected based on the size of the objects being separated. In at least one embodiment, the size of the pores is selected such that the pores are large enough not to trap the objects, but small enough to expose the objects to the greatest magnetic field gradient possible. For example, when a suspension comprises particles that are 1 µm in diameter, the pore size may be 4 µm in diameter. In at least one embodiment, the pore size is about 2 to 5 times the size of the target object. For example, when trapping exosomes, which generally range in size from 30 nm to 200 nm, the pore size can range from about 50 nm to 1 µm. Larger pore sizes may also be used depending on the size of the target particles or to prevent co-purification of other particles present in the sample caused by trapping due to particle size. For example, a pore size of 500 nm would trap any particles in a sample greater than 500 nm based on the inability of those particles to pass through the pores. To reduce trapping of unwanted particles, it may be desirable to use a larger pore size. To counter the reduction in trapping the desired particles, additional filters can be used in series.

Due to the different manner in which the pores are formed, the pore sizes of TEMPO/TENPO filters can be significantly smaller than the pore sizes of MagNET filters. Ion-track etching currently allows for the formation of pore sizes as small as 15 nm, whereas currently electroforming technology allows for the formation of pore sizes on the scale of a few micrometers.

The pores within the membrane may have any cross-sectional shape, such as, for example, circular, oval, rectangular, square, or other polygonal shape. In TEMPO/TENPO filters, the pores are generally circular in shape. The pore shape influences the magnetic field gradient. In at least one embodiment, the pores have a symmetrical geometry. According to at least one embodiment, the pores have a circular cross-section. Without wishing to be limited by theory, it is believed that a circular cross-section provides the most uniform magnetic field gradient.

The shape of the pores may affect the efficiency of the magnetic separation filter. As discussed below, capture of magnetic particles occurs when the particle enters the magnetic field of the magnetic separation filter, which is strongest at the edge of the filter. An elongated pore, such as an oval or rectangular pore may increase the edge density of the pores in the device by increasing the effective length of the edge for a given number of pores, as compared to circular or square pores. Therefore, in accordance with at least one embodiment, the pore shape may be selected to maximize the edge density of the magnetic separation filter.

The magnetic separation filters according to the present invention may allow for much greater flow rates than other available separation devices, such as microfluidic devices, which run at 1 ml/h. In exemplary devices prepared by the inventors, TEMPO/TENPO filters have been prepared with a throughput up to about 40 ml/h with high enrichment. The inventors have made MagNET filters having a throughput of 180 ml/h with an enrichment greater than $10^3$.

The magnetic separation devices according to embodiments of the present invention may be flexible. Flexibility of the magnetic separation device can be beneficial in the construction of microfluidic devices. Rigid devices, such as those constructed of silicon, may be difficult to manipulate within the confines of small structures, such as those found in microfluidic devices.

Another aspect of the present disclosure relates to a microfluidic or nanofluidic device comprising a magnetic separation device.

In at least one embodiment, the microfluidic/nanofluidic device comprises at least one lateral flow channel and at least one vertical flow magnetic separation filter. The vertical flow magnetic separation filter, such as, for example, a TEMPO/TENPO filter or MagNET filter, which comprises a membrane having a plurality of pores, a layer of magnetically soft material disposed on the membrane, and a passivation layer disposed on the layer of magnetically soft material.

The microfluidic/nanofluidic device may comprise any known structural or functional element. In at least one embodiment, the microfluidic/nanofluidic device can be modular, including the vertical flow magnetic separation filter.

In at least one embodiment, the microfluidic/nanofluidic device comprises a plurality of vertical flow magnetic separation filters. Because each additional vertical flow magnetic separation filter increases the enrichment, $\xi$, one of ordinary skill in the art would recognize that the number of vertical flow magnetic separation filters can be selected to achieve the desired level of enrichment. In at least one embodiment, the microfluidic/nanofluidic device comprises from 2 to 10 vertical flow magnetic separation filters, such as, for example, from 2 to 4. In other embodiments, the microfluidic/nanofluidic device could contain more than 10 vertical flow magnetic separation filters.

The plurality of vertical flow magnetic separation filters can be arranged in series. In at least one embodiment, each of the plurality of vertical flow magnetic separation filters has a membrane containing pores and a pore density that are similar. In other embodiments, each of the vertical flow magnetic separation filters may have different pore sizes and/or pore densities. In at least one embodiment, the microfluidic/nanofluidic device may comprise a plurality of TEMPO/TENPO filters or a plurality of MagNET filters. In other embodiments, the microfluidic/nanofluidic device may combine at least one TEMPO/TENPO filter and at least one MagNET filter.

According to at least one embodiment, the microfluidic/nanofluidic device may comprise a flow converter for redirecting the lateral flow in the at least one lateral flow channel to vertical flow in the at least one vertical flow magnetic separation filter. The flow converter may comprise, for example, a plurality of pathways through which fluid can pass from the lateral flow channel to the vertical flow magnetic separation filter. Each of the plurality of pathways, for example, may be of similar length, such that fluid passing through the microfluidic/nanofluidic device will have the same residence time regardless of the path through which the fluid flows. In at least one embodiment, the flow converter comprises a symmetric branched geometry.

A microfluidic/nanofluidic device according to an embodiment of the present disclosure is shown in FIG. 1c. The microfluidic/fluidic device comprises an acrylic substrate, a lower 200 µm mylar layer, a TEMPO/TENPO filter, a flow converter comprising a layer of 50 µm mylar film having 16 regularly spaced holes and a layer of 200 µm mylar film having a symmetric branched geometry in fluidic communication with the 16 regularly spaced holes and fed by a lateral flow channel, and a top layer of 50 µm mylar film.

Another aspect of the present disclosure relates to a method for separating magnetically tagged particles in a microfluidic/nanofluidic device.

In at least one embodiment, the method comprises exposing a vertical flow magnetic separation filter to an external magnetic field to induce a magnetic field gradient within pores of a membrane in the vertical flow magnetic separation filter, flowing a suspension comprising magnetically tagged particles through a lateral flow channel in a microfluidic/nanofluidic device, capturing the magnetically tagged particles in the pores of the vertical flow magnetic separation filter, removing the external magnetic field, and releasing the captured magnetically tagged particles.

The magnetically tagged particles may comprise, for example, cells, exosomes, molecules, nucleic acids, proteins, polypeptides, or another taggable object of interest. In accordance with at least one embodiment, the magnetic separation filter can be used for the diagnosis of conditions or diseases, such as cancer or brain injury, by capturing magnetically tagged particles, such as exosomes. Exosomes contain protein biomarkers as well as fragments of mRNA, μRNA, and DNA from their mother cells. These biomarkers can be used to determine whether a subject has a specific condition. For example, a TEMPO/TENPO filter as described above may be used to isolate one or more exosomes. Because most cells secrete exosomes, the method according to the present disclosure may be used to detect more than one condition simultaneously. Exosomal biomarkers may be tagged with magnetic nanoparticles (MNPs), such as iron oxide nanoparticles or any other MNP known in the art, and trapped by a magnetic separation filter according to an embodiment disclosed herein (e.g., a TEMPO/TENPO filter). For example, the exosomes may be incubated with a cocktail of biotinylated antibodies and subsequently incubated with anti-biotin MNPs.

Exosomes trapped by the magnetic separation filter may be evaluated by analyzing the nucleic acids or proteins extracted from the exosomes, e.g., by using qPCR.

According to at least one embodiment, multiple biomarkers may be used to enable the method to detect more than one condition or disease.

Conditions or diseases that may detected include any condition or disease which can be detected by biomarkers contained in an exosome, such as cancer (including pancreatic cancer, prostate cancer and glioblastomas), addiction, tuberculosis, or brain injuries (including ischemic brain injury and traumatic brain injury). For example, brain-derived exosomes have been found in the bloodstream after brain injury. The method according to the present invention can be used to isolate and identify these exosomes. According to at least one embodiment, the exosomes may be isolated from samples including blood/serum samples or other fluids, such as, urine.

EXAMPLES

TEMPO Filter

To demonstrate the utility of this platform, a chip with a 5 μm pore size TEMPO was used to efficiently isolate immunomagnetically labeled *E. Coli* from a suspension of similarly sized bacteria for subsequent downstream analysis.

The TEMPO filter comprises a dense array (~2000/mm$^2$) of track-etched micropores coated with a thin layer of soft magnetic material (FIG. 1a). The micropores create large gradients $\nabla B$, which imparts strong magnetic forces F~$(B \cdot \nabla)B$ on magnetic nanoparticle *MNP) labeled cells as they pass through the pores. Targeted cells are trapped and isolated from the unlabeled cells which flow through the filter unimpeded. The chip sits in a large uniform magnetic field $|B|=0.2$ T, provided by a small external neodymium iron boron (NdFeB) magnet. This field magnetized both the MNP labeled cells and the TEMPO filter. When the NdFeB magnet is removed, the force disappears and the trapped cells can be efficiently released.

Microfluidic Chip

A microfluidic chip was fabricated by integrating the TEMPO filter into a microfluidic network. To fabricate the TEMPO filter, flexible track etched films (Whatman Nuclepore) were coated with soft magnetic material (200 nm, $Ni_{20}Fe_{80}$) and a passivation layer (30 nm, Au) using thermal evaporation. The metals are thermally evaporated using a Kurt Lesker (PVD-75) e-beam/thermal evaporator in the Wolf Nanofabrication Facility at University of Pennsylvania. FIG. 1d shows an SEM micrograph of a 5 μm diameter micropore TEMPO filter, with the gold, $Ni_{20}Fe_{80}$, and polycarbonate layers visible.

The TEMPO filter was integrated into laser-cut laminate sheet microfluidics (FIG. 1c). The microfluidic chip was designed to evenly distribute fluid to the TEMPO filter, such that optimum sorting efficiency can be achieved. A "shower head" geometry was utilized (FIG. 1c), in which flow in a lateral microchannel was converted into an evenly distributed vertical flow. The flow was split evenly to sixteen 0.5 mm$^2$ holes above the TEMPO filter using a symmetric branching geometry. Underneath the TEMPO filter was a thick (200 μm) channel that brought the fluid to the output. The microfluidic channel patterns were defined using laser-cutting (VLS3, VersaLaser). The base was constructed using 1.5 mm thick extruded poly(methyl methacrylate) sheet (McMaster Carr). The device was coupled to blunt syringe tips (McMaster Carr) epoxied onto the top layer of the microfluidic chip to control flow through the chip. The device was pre-treated with Pluronic F-127 (Sigma-Aldrich) to minimize non-specific retention of cells to the channel walls or to the TEMPO filter.

Immunomagnetic Labeling of Bacteria

To demonstrate the utility of the TEMPO filter, immunomagnetically labeled bacteria were efficiently sorted from a heterogeneous suspension. An indirect labeling method was utilized in which the bacteria were first targeted with biotinylated antibody and subsequently tagged with anti-biotin MNPs. Nuclear Magnetic Resonance (NMR) measurements (Bruker Minispec) on the labeled cells revealed that there were 2300 particles per cell.

The samples were prepared mixing a known quantity of *E. coli* and *S. Aureus*. Fresh *E. coli* bacteria samples (Invitrogen) were grown overnight in Luria-Bertain (LB) broth (10 g of tryptone, 5 g of yeast extract, and 10 g of NaCl/L) at 37° C. in 14 mL round-bottom tubes with rotary shaking for about 6 hours. The concentrations of the *E. coli* bacteria stock solutions were quantified by a Varian Cary 100 Bio UV-Visible Spectrophotometer. The cells were harvested at a concentration equivalent to an optical density at 600 nm value of 0.73 (~$7.3 \times 10^8$ cell/ml). The bacterial cells were then used for further experiments immediately.

The following steps were taken to magnetically label the cells. The *E. coli* stock sample was diluted to concentration range of $1 \times 10^7$-$9 \times 10^7$ cell/ml with buffer (0.5% bovine serum albumin and 2 mM EDTA in phosphate-buffered saline, Fisher Scientific). *S. Aureus* pre-labeled with Alexa Fluor 594 were utilized. Biotinylated anti-*E. coli* polyclonal antibody (80 μl, 3.2 mg/ml, Thermo Scientific) and the diluted *E. coli* bacterial sample (80 μl, $1 \times 10^7$-$9 \times 10^7$ cell/ml) were mixed and incubated at room temperature for 1 hour. After that, the sample was washed twice by the buffer. Anti-biotin nanoparticles (20 μl, Miltenyi Biotec) were added into the sample and incubated at 4° C. for 15 minutes.

The sample was subsequently centrifuged at 1100 rcf for 10 minutes. The bacteria pellet was resuspended in 500 μl buffer. Unlabeled *E. coli* bacteria samples were set as a control. The nanoparticle conjugated bacteria sample and control were measured by a Bruker Minispec MQ60 NMR analyzer to quantify labeling. For fluorescence detection, SYTO9 stain (500 ml, 10 μM, Life Technologies) was added into the nanoparticle conjugated bacteria sample and 15 minutes room temperature incubation was allowed. The sample was then washed 3 times with PBS to remove residual stain.

Characterization

Finite Element Simulations

Figure 2:
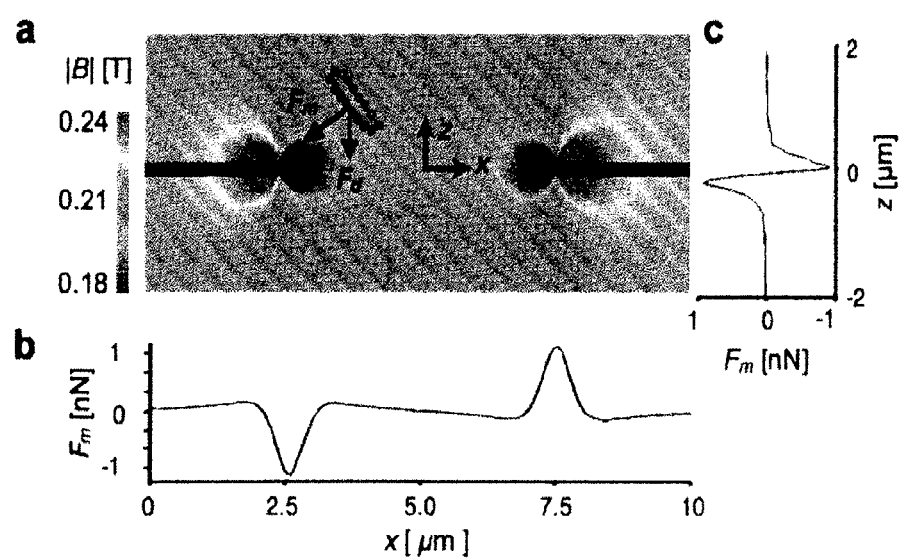
FIG. 2 is a is a graphical representation of (a) a magnetic field simulation of a pore within a magnetic separation device according to an embodiment of the present invention; (b) the magnetic force on a 1 μm diameter magnetic microbead plotted as a function of x Δz=500 nm above a magnetic separation device; and (c) the magnetic trapping force plotted against z Δx-500 nm from the edge of a micropore.

Magnetic field simulations were used to aid the design and characterization of the TEMPO filter. The simulated magnetic field strength B is plotted on the cross-section of the self-assembled magnetic filter (FIG. 2a). The magnetic field strength drops rapidly in distance from the surface of the magnetic layer, creating large gradients that least to strong magnetic forces. The simulation geometry was an axially symmetric membrane with a 5 μm pore, coated with 200 nm of $Ni_{20}Fe_{80}$. One inch below the TEMPO filter was a fully magnetized NdFeB magnet $M_p$=875 kA/m. Finite element simulations (Maxwell, Ansoft) were used to simulate the magnetic field B, from which the magnetic force $F_m$ was calculated.

The magnetophoretic force $F_m$ on cells is calculated by combining the finite element simulation from FIG. 2a with the magnetic model described above. FIG. 2b shows the force that a 1 μm diameter iron oxide loaded bead experiences versus the lateral distance from the pore's edge, 500 nm above the TEMPO filter surface. The simulation shows that the force is localized within ~2 μm of the pore's edge. The ability of the pore to capture passing cells is therefore optimized when the pore diameter is as small as possible, while still being large enough to pass non-targeted objects.

Once a cell is brought to the edge of the pore, the competition of the magnetic trap and the drag force from the passing fluid determine whether the cell gets trapped. The drag force is given by Stokes' law ($F_d$=6πμaV, where μ=0.8 mPa*s is the viscosity of water. The average velocity can be calculated through the pores $v_{avg}$=Φ/(ρ$A_p$A) where ρ=$10^6$ pores/$cm^2$ is the pore density (Whatman), $A_P$ is the cross sectional area of an individual pore, and A=0.39 $cm^2$ is the cross-sectional area of the membrane. The flow profile through a single pore v∝$(1-(r/a)^2)^{1/2}$ can be calculated based on the Stokes' equations of motion. The flow velocity is greatest in the center of the pore, and therefore the drag force $F_d$ is minimal at the edges of the pore where the cells are trapped. The magnetic force $F_m$ in the z direction that resists the flow is shown in FIG. 2c. A line was it to the force curve in FIG. 2b and the effective spring constant of the trap is found to be k=12.3 nN/μm. Once trapped, a 1 μm magnetic bead as modeled above, will remain trapped at flow rates Φ>100 ml/hr.

Experimental Characterization

Figure 3A:
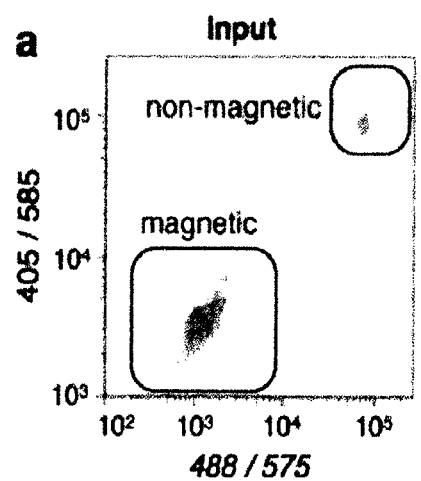
FIG. 3a is a flow cytometry quantification of bead population before filtration according to an embodiment of the present invention.
Figure 3B:
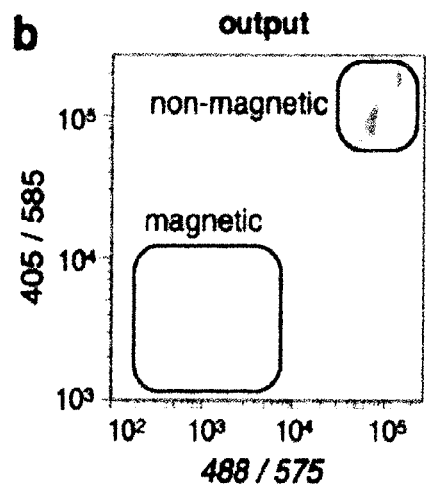
FIG. 3b is a flow cytometry quantification of bead population after filtration according to an embodiment of the present invention.

The efficiency of the TEMPO filter was first tested by sorting magnetic from non-magnetic polystyrene beads. A suspension that contained both 1 μm diameter fluorescent polystyrene beads (FluoSpheres® Polystyrene Microspheres, 1.0 μm, Invitrogen) and 1 μm diameter fluorescent magnetic beads (screenMAG, Chemicell) was pumped through the TEMPO filter. The input (FIG. 3a) and output (FIG. 3b) were measured using flow cytometry (LSR II, BD), and the efficiency of the TEMPO filter was analyzed. The three parameters of the magnetic sorting device that were characterized include enrichment $\xi=(C_{1p}/C_{1m})/(C_{0p}/C_{0m})$, purity $C_{0m}/C_{0p}$, and flow rate Φ, where $C_{0p}$ and $C_{1p}$ are the concentration of non-targeted cells before and after sorting, respectively, and $C_{0m}$ and $C_{1m}$ are the concentration of targeted cells before and after sorting, respectively.

Figure 3C:
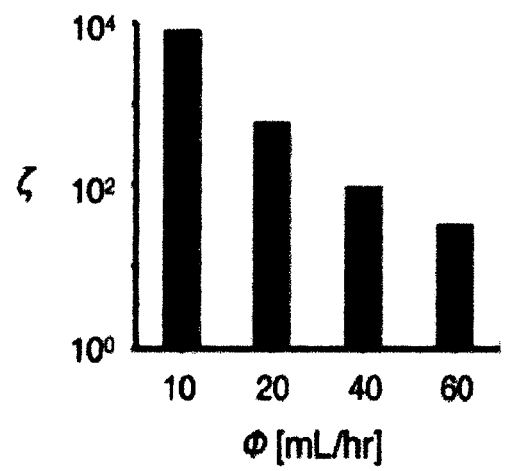
FIG. 3c is a graph of enrichment, ξ, as a function of flow rate, Φ, according to an embodiment of the present invention.
Figure 3D:
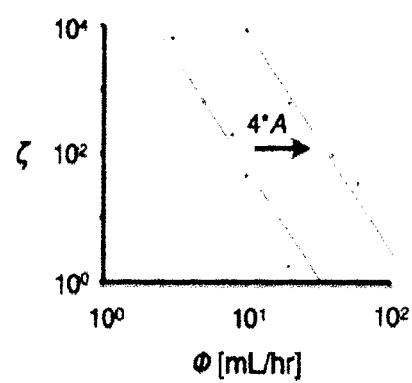
FIG. 3d is a graph showing the effect of surface area on the enrichment, ξ, as a function of flow rate, Φ, according to an embodiment of the present invention.

The TEMPO filter achieved high sorting efficiency at flow rates as great as 60 l/hr (FIG. 3c). The sorting efficiency was observed to be a function of flow rate, following a power law dependency, Φ∝$\xi^m$, where m=-3.74 ($R^2$=99.9%) over several orders of magnitude. By increasing the area of the filter from A=0.6×0.6 $cm^2$ to an area 4 times larger, the enrichment curve shifted to the right in flow rate Φ by an amount linearly proportional to the increase in A (FIG. 3d). The power law shifted, but its slope m remained the same, suggesting that the power law dependency comes from an intrinsic property of the micropore geometry. The scaling of the flow rate Φ with the area A of the filter, allows chips to be designed with a large range of flow rates appropriate for specific applications.

To further increase enrichment, several TEMPO filters can be placed in series. The TEMPO filters are placed in series by being stacked vertically, utilizing a slight modification to the fabrication strategy that is used for the single filter devices. There is one layer of 200 μm thick laser cut mylar between each TEMPO filter. Additional flow splitters are not necessary for each TEMPO layer, as the flow remains evenly distributed as it passes through the vertically integrated filters.

Figure 4A:
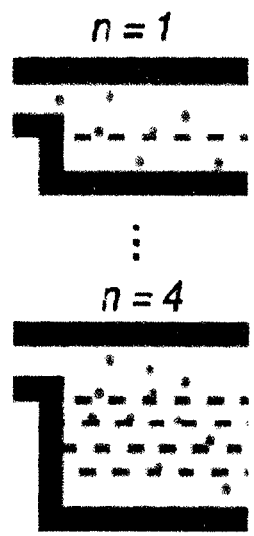
FIG. 4a shows schematic representations of a microfluidic device comprising a single vertical flow magnetic separation filter and a microfluidic device comprising four vertical flow magnetic separation filters connected in series, according to an embodiment of the present invention.
Figure 4B:
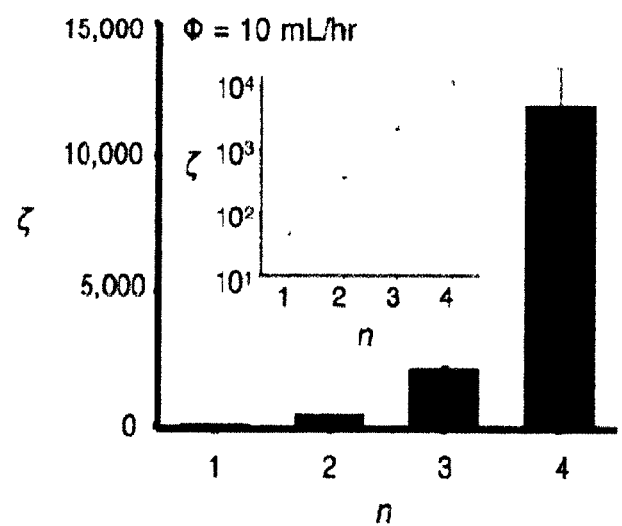
FIG. 4b is a graph showing the effect of the number of vertical flow magnetic separation filters connected in series on the enrichment, ξ, as a function of the number of filters in series, according to an embodiment of the present invention.

There is an exponential increase observed in sorting efficiency for each additional TEMPO filter (FIG. 4a). The exponential increase is understood by assuming that each filter enriches its input by an amount $\xi_0$, independent of any of the other filters. If each subsequent filter receives the previous filter's output as its input, then the enrichment after n stages is $\xi=(\xi_0)^n$. To test this effect, the enrichment $\xi$ of four different chips, with n=1, 2, 3, and 4 filters was measured (FIG. 4b). The enrichment $\xi$ fits well to an exponential $\xi \propto e^{bn}$, with b=1.84 ($R^2$=99.8%). This exponential growth allows for large improvements in enrichment to be made by adding additional filters. For instance, by increasing n=1 to n=4 for an A=0.36 $cm^2$ TEMPO at Φ=10 ml/hr, enrichment was improved 250×.

Figure 5A:
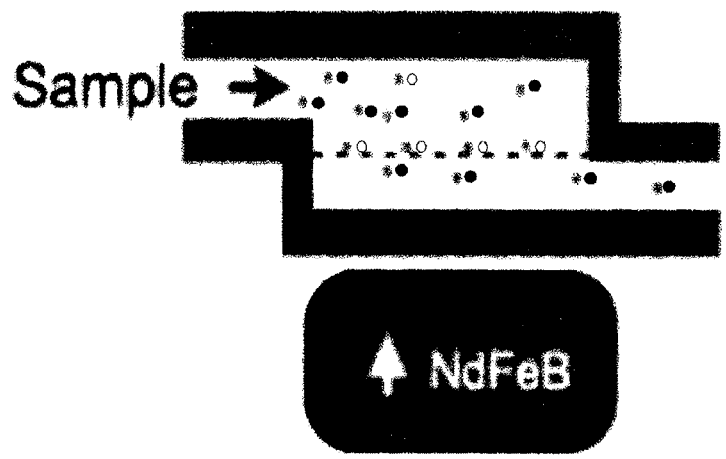
FIG. 5a-5c is a schematic representation of the trapping and releasing of magnetically tagged particles in a microfluidic device comprising a vertical flow magnetic separation filter, according to an embodiment of the present invention.
Figure 5B:
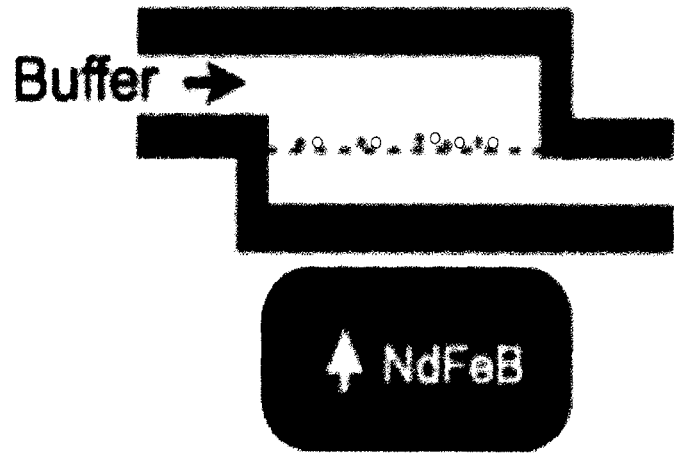
Figure 5C:
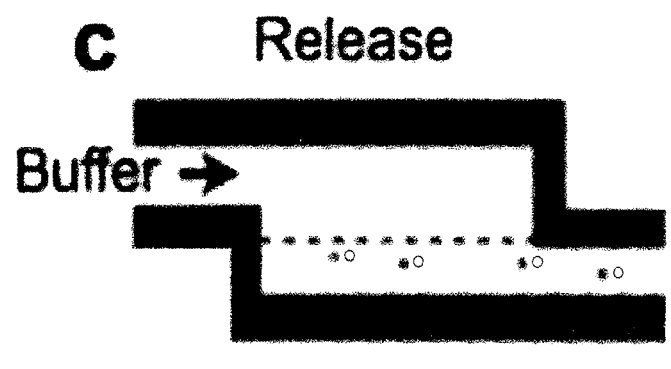
Figure 5D:
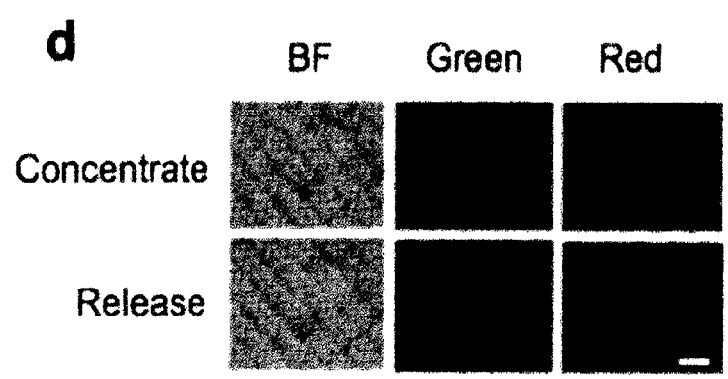
FIG. 5d is a fluorescence micrograph of cells on a vertical flow magnetic separation filter during capture and after release, according to an embodiment of the present invention.
Figure 5E:
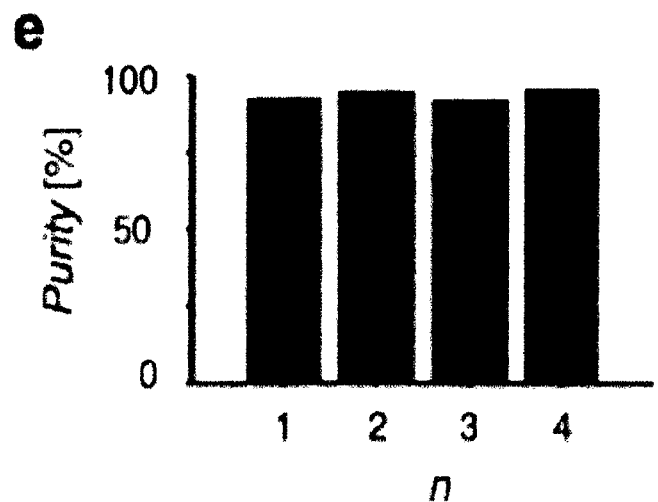
FIG. 5e is a graph of the purity of captured and released beads as a function of the number of vertical flow magnetic separation filters connected in series, according to an embodiment of the present invention.

Release of cells is important for applications where downstream analysis is desired on whole cells, such as immunostaining or single cell genotyping. The TEMPO filter has the advantage that when the external magnet is removed, the magnetic force disappears and the trapped cells can be released. This feature is facilitated by the low magnetic remanence of $Ni_{20}Fe_{80}$, which brings the magnetization to zero when the external magnet is taken away. The trap and release protocol is outlined in FIG. 5. First, the targeted cells (open circles ○) are trapped and concentrated by passing the sample through the TEMPO filter with the external magnet in place (FIG. 5a). Next, cells and debris (closed circles ●) that were not trapped are washed away by passing buffer solution through the TEMPO filter with the external magnet still in place (FIG. 5b). Finally, the external magnet is removed and the trapped cells are released into the passing buffer solution (FIG. 5c). To demonstrate this functionality, magnetic beads were trapped from a suspension of non-magnetic beads, washed, and then subsequently released (FIG. 5d). The purity of the output of the release beads was quantitatively measured (>95%) and did not significantly change with additional layers of TEMPO (P>0.5, two-tailed t test) (FIG. 5e).

Figure 6A:
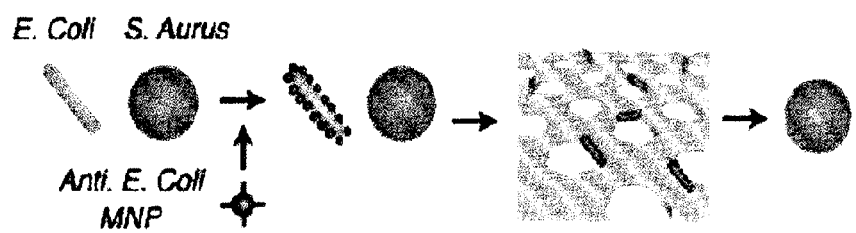
FIG. 6a is a schematic representation depicting the capture of magnetically tagged bacteria by a vertical flow magnetic separation filter, according to an embodiment of the present invention.
Figure 6B:
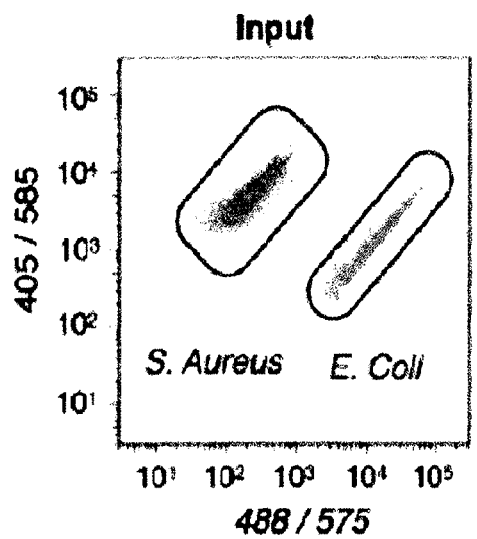
FIG. 6b is a flow cytometry quantification of cell population before filtration according to an embodiment of the present invention.
Figure 6C:
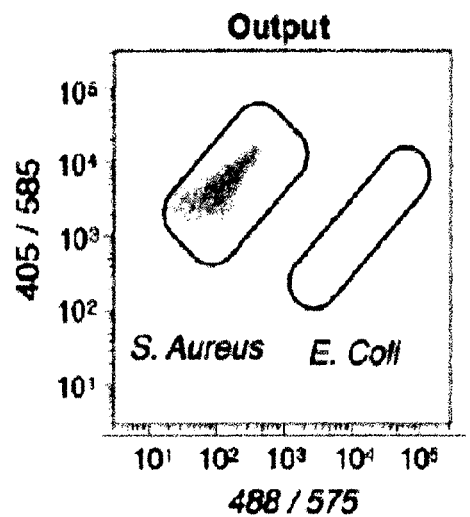
FIG. 6c is a flow cytometry quantification of cell population after filtration, according to an embodiment of the present invention.

The ability of the TEMPO filter to sort bacterial cells was demonstrated by magnetically capturing *E. coli* bacteria from a suspension of *S. Aureus*, based on an anti-*E. coli* antibody (FIG. 6a-6c). A TEMPO with n=3 filters and an area A=0.6×0.6 cm² was used. The change in the composition of the suspension before and after filtration was measured by flow cytometry. The input (FIG. 6b) and output (FIG. 6c) were measured using flow cytometry, and the sorting efficiency of the TEMPO was analyzed. At a flow rate of Φ=1 ml/hr, enrichment of ξ=450 was achieved. Flow rates and enrichment rates could be increased further by enlarging the area of the filter A or the number of filters n, as was shown above.

Background Insensitivity

To demonstrate background insensitivity, prepared *E. coli* and *S. aureus* samples were spiked into multiple samples (phosphate buffer saline (PBS), PBS with excess MNPs ($10^8$/ml), oral lavage from a healthy volunteer, and local river water). The oral lavage was collected by having a healthy volunteer rinse his mouth for 30 s with sterile saline solution. The river water was collected from the Schuylkill River in Philadelphia, Pennsylvania. For each test, 1 ml of each sample was spiked with $8 \times 10^5$ *E. coli* and $6 \times 10^4$ *S. aureus*.

Oral lavage is commonly used for the diagnosis of oral infections, and samples include a heterogeneous suspension of bacteria including *A. actinomycetemcomitans* (Aa), *p. gingivalis* (Pg), *T. forsythensis* (Tf), *P. intermedia* (Pi), and *M. micros* (Mm). The observed enrichment ξ from oral lavage and in PBS was statistically identical (P>0.5, a two-tailed t-test), verifying that the complex background of the clinical samples had a negligible effect on TEMPO sorting. Further comparisons were made on samples with excess MNPs ($10^8$ particles per ml) and on an environmental sample from the Schuylkill River. In both cases, the measured enrichment was found to be statistically identical (P>0.5, a two-tailed t-test) to that measured in PBS.

Figure 6D:
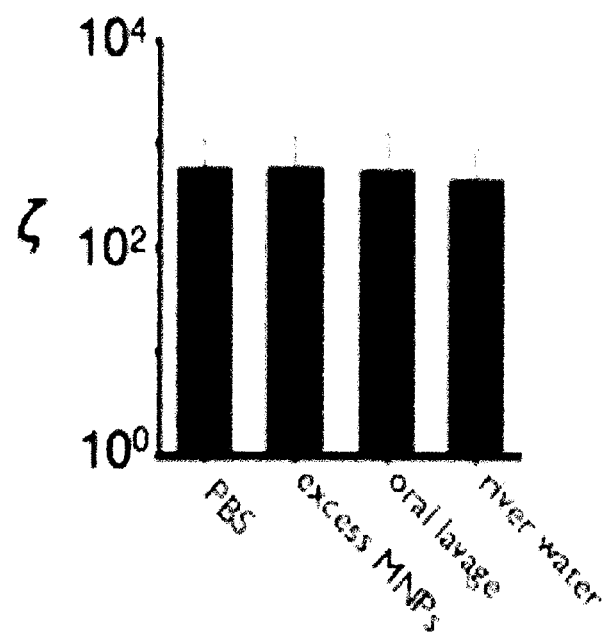
FIG. 6d is a graph comparing the enrichment for various samples, according to an embodiment of the present invention.

Both the clinical and environmental sample contained particulates larger than the pore size of the TEMPO (d=5 μm). However, due to the large density of micropores ($\rho=10^6$ cm$^{-2}$), the blockage of a few pores did not significantly change the behavior of the device. Additionally, due to the use of magnetic sorting, the MNP-labeled cell could be sorted directly from the unprocessed clinical and environmental sample without interference from salinity, turbidity, or pH. FIG. 6d shows the enrichment for each of the samples.

Separation of Circulating Tumor Cells (CTCs)

Figure 7A:
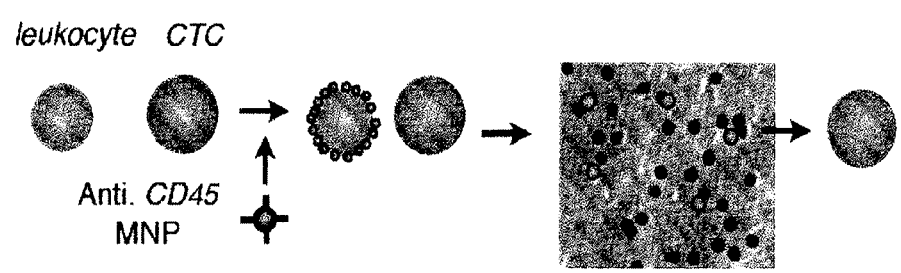
FIG. 7a is a schematic representation depicting the capture of magnetically labeled circulating tumor cells by a vertical flow magnetic separation filter, according to an embodiment of the present invention.
Figure 7B:
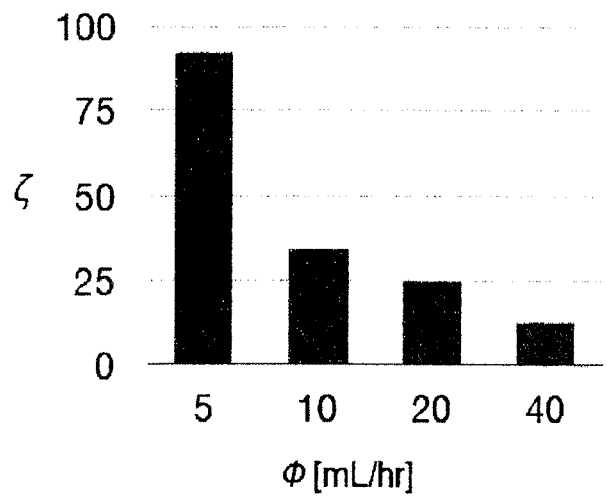
FIG. 7b is a graph of enrichment, ξ, as a function of flow rate, Φ, according to an embodiment of the present invention.
Figure 7C:
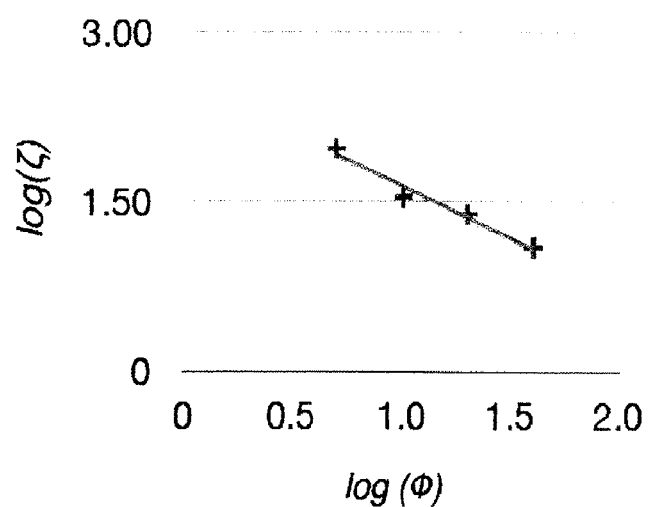
FIG. 7c is a graph of log ξ as a function of log Φ, according to an embodiment of the present invention.

Isolation of CTCs from a background of leukocytes was studied using a 30 μm pore size TEMPO filter. CTCs were labeled with Anti. CD45 MNPs and separated with the TEMPO filter (FIG. 7a). The enrichment followed the same patterns as when smaller particles and a smaller pore size was used (see FIGS. 7b and 7c).

ExoTENPO Chip Fabrication

Figure 26:
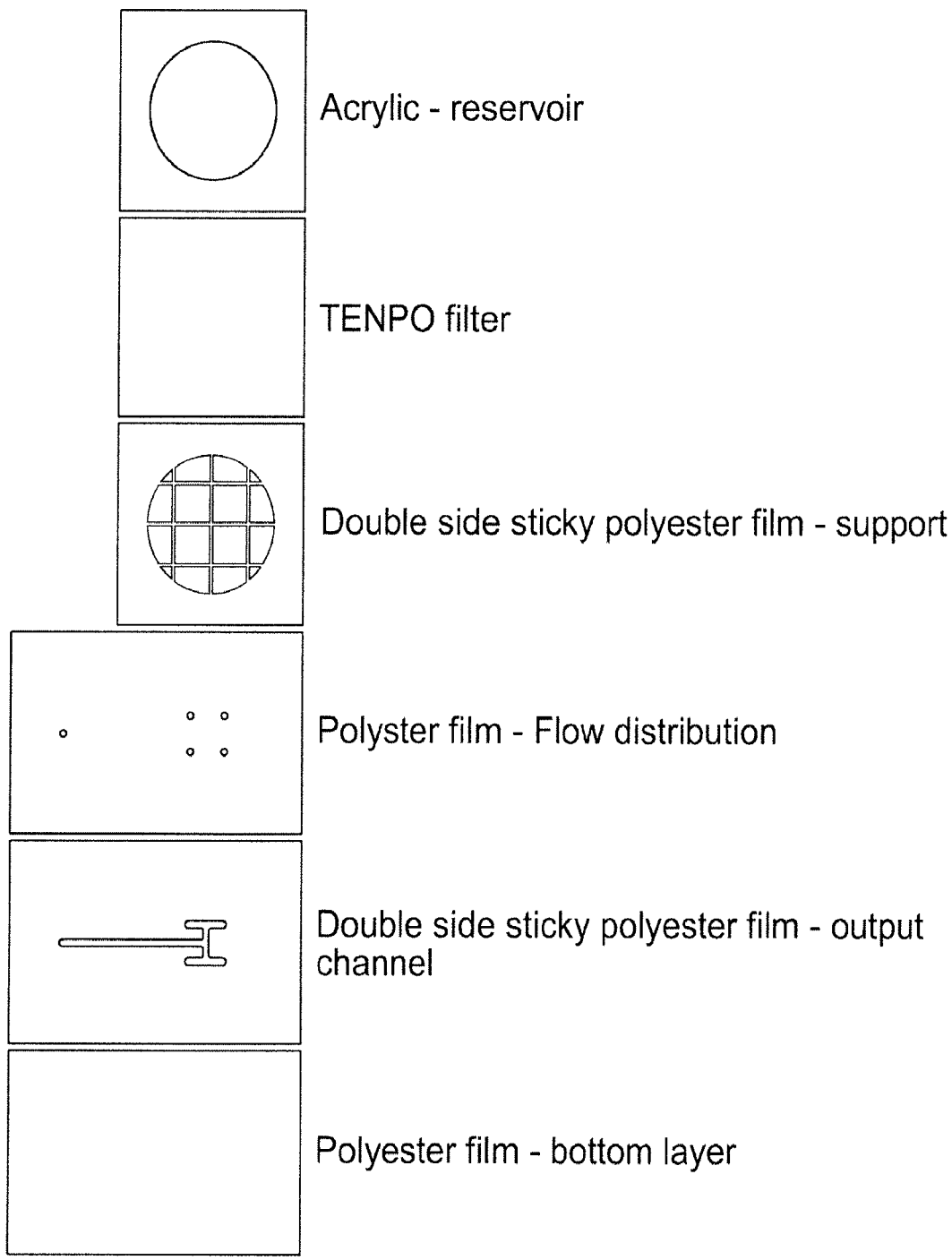
FIG. 26 shows an ExoTENPO device according to one embodiment layer by layer. The top part is the reservoir made of acrylic that can hold samples, which travel through the ExoTENPO filter. Support prevents the filter from sagging. A showerhead design distributes the flow evenly for the output channel.

The ExoTENPO filters were fabricated by thermally evaporating (Kurt Lesker PVD-75, Singh Nanofabrication Facility, University of Pennsylvania) 200 nm layer of permalloy ($Ni_{20}Fe_{80}$) onto the surface of a track-etched polycarbonate membrane (Whatman). A 30 nm layer of gold was subsequently deposited to prevent oxidation of the permalloy. The ExoTENPO membranes were incorporated into a laminate sheet microfluidic device fabricated by laser micromachining (Universal Laser VLS 3.50) sheets of moisture-resistant polyester film (McMaster-Carr, 0.004" thick) and solvent-resistant tape (McMaster-Carr) (FIG. 26) An optically clear cast acrylic sheet (McMaster-Carr) was used to form a reservoir for the input, and the output was made using a polydimethylsiloxane (PDMS) piece, pressure-fit to tygon tubing to connect to a negative pressure supply (Programmable Syringe Pump, Braintree Scientific).

Characterization of ExoTENPO Performance

Figure 21D:
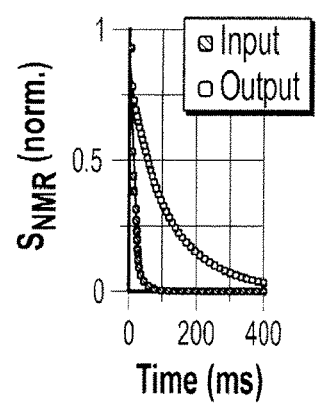
FIG. 21d shows the capture of particles by an ExoTENPO according to one embodiment, the T2 relaxation time of the proton NMR $S_{NMR}$ of the suspension is measured for the input and the output.
Figures 21E, 21F, 21G:
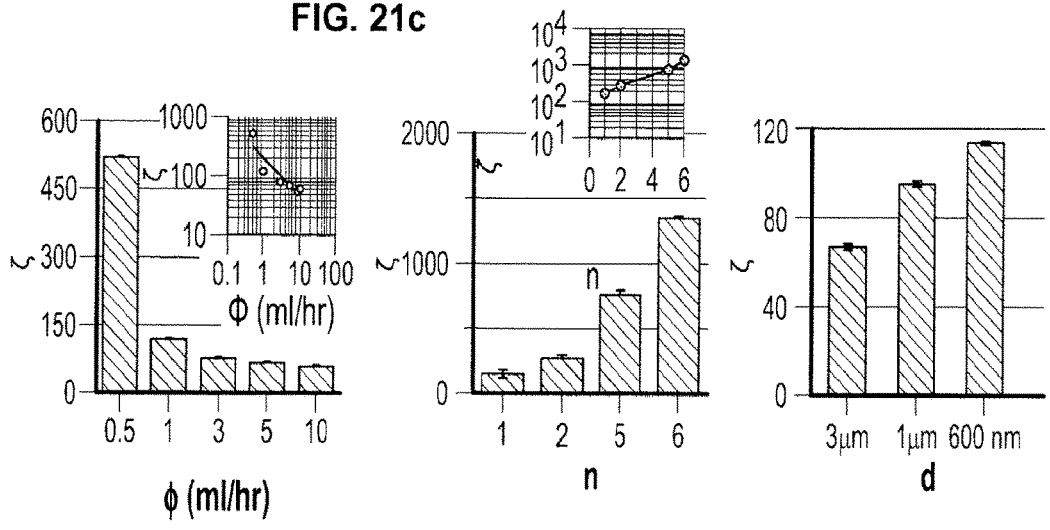
FIG. 21e shows the enrichment ζ of the magnetic beads is measured versus flow rate φ. Inset: Enrichment vs. flow rate on a log-log plot.
FIG. 21f shows the enrichment vs. number of ExoTENPO membranes in series n according to one embodiment. Inset: Enrichment vs. n on a log-linear plot.
FIG. 21g shows the enrichment vs. pore size, for a d=3 μm, 1 μm, and 600 nm pore ExoTENPO according to one embodiment.

To experimentally characterize an ExoTENPO filter's capability to isolate nanoscale magnetic objects at various flow rates, a simple model system was used consisting of 50 nm iron oxide magnetic nanoparticles (MNPs) (Miltenyi Biotec) that have a uniform and known diameter and magnetization. To determine the concentration of nanoparticles the nuclear magnetic resonance $T_2$ relaxation time was measured (Bruker mq60 MR relaxometer) operating at 1.41 T, (FIG. 21d) making use of the fact that the concentration of MNPs $C_{MNP}$ is proportional to $1/T_2 \propto C_{MNP}$. The metric that was used to evaluate the performance of the chip is the fraction of MNPs that the chip captures $\zeta = C_{i,MNP}/C_{o,MNP}$ at a given flow rate φ, where $C_{i,MNP}$ is concentration of MNPs in the input and $C_{o,MNP}$ is concentration in the flow-through. As expected based on finite element simulations, the capture rate of MNPs decreased as flow rate increased (FIG. 21e). The capture rate ζ decreased as a function of the flow rate φ as a power law $\zeta = \phi^m$, m=−0.65. As predicted, the capture rate ζ could be recovered at high flow rates φ by stacking multiple layers n of the ExoTENPO membranes in the chip. (FIG. 21f) The capture rate ζ was found to increase exponentially with the number n of ExoTENPO. This exponential increase (FIG. 21f-inset) arises from the fact that each layer of ExoTENPO has an independent probability of capturing each exosome, and thus the probability of an exosome being captured by multiple ExoTENPOs in series compounds with the passage through each subsequent ExoTENPO in series. By placing n=6 ExoTENPO in series, an extremely high capture rate ζ>1,000 was achieved at a flow rate sufficient for running clinical samples φ=10 mL/hr. It was verified that as the pore size was decreased from d=3 μm to d=600 nm, there was a significant increase in the capture rate ζ (FIG. 21g). To validate that the ExoTENPO isolated exosomes primarily due to magnetic trapping, a negative control experiment was performed by turning off the magnetophoretic force by removing the external NdFeB magnet, which resulted in no exosomes captured ζ=1.

Magnetic Exosome Isolation for Prognosis of Pancreatic Cancer

Early detection of cancers can significantly reduce mortality. Pancreatic cancer is the fourth most common cause of cancer related death in the United States, with a five year survival rate of only 8%. Because pancreatic tumor cells are localized in difficult to access parts of the body, molecular measurements currently rely on invasive procedures (i.e. biopsy) which severely limit their practical diagnostic use. Nano-scale vesicles that originate from tumor/injured cells and which can be found circulating in the blood (e.g. exosomes) have been discovered to contain a wealth of proteomic and genetic information to monitor cancer progression, metastasis, and drug efficacy.

However, the use of exosomes as biomarkers to improve patient care has been limited by fundamental technical challenges that stem from extreme scarcity and the small size of tumor-derived exosomes (30 nm-200 nm) and the extensive sample preparation (>24 hr) required prior to measurement.

Figure 16:
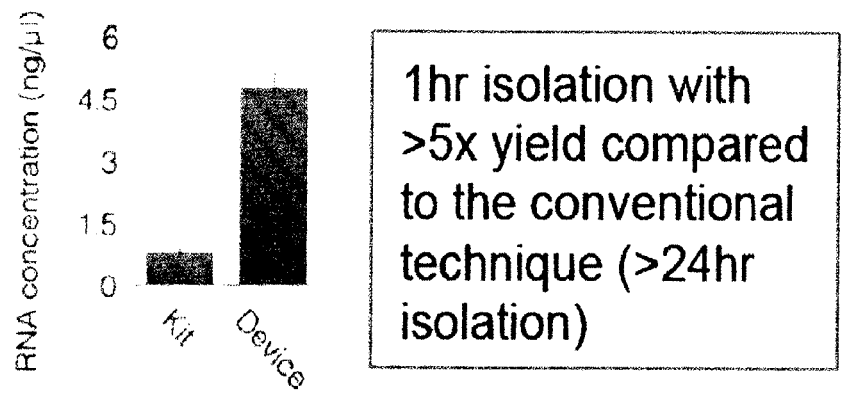
FIG. 16 shows a graph of the RNA concentration in isolated exosomes using a magnetic separation device in accordance with an embodiment of the present invention compared to a convention.

To address these challenges, exosomes were detected using a TEMPO filters in accordance with embodiments of the present invention, which combined the benefits of nanoscale sorting with extremely fast flow rates (<1 hr assay time). The unbiased exosome detection achieved >5× yield compared to the conventional technique (ultracentrifugation) (see FIG. 16). Using linear discriminant analysis (LDA), different groups of mice were classified (cancer vs. healthy). And more importantly, it was possible to distinguish pre-cancer mice from healthy mice.

Figure 17:
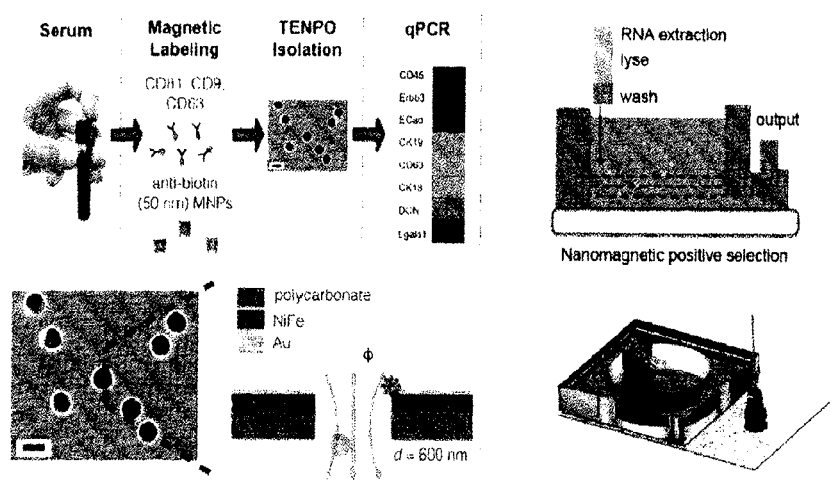
FIG. 17 shows a schematic representation of process for isolating exosomes and extracting RNA using a TEMPO filter in accordance with an embodiment of the present invention.
Figure 18:
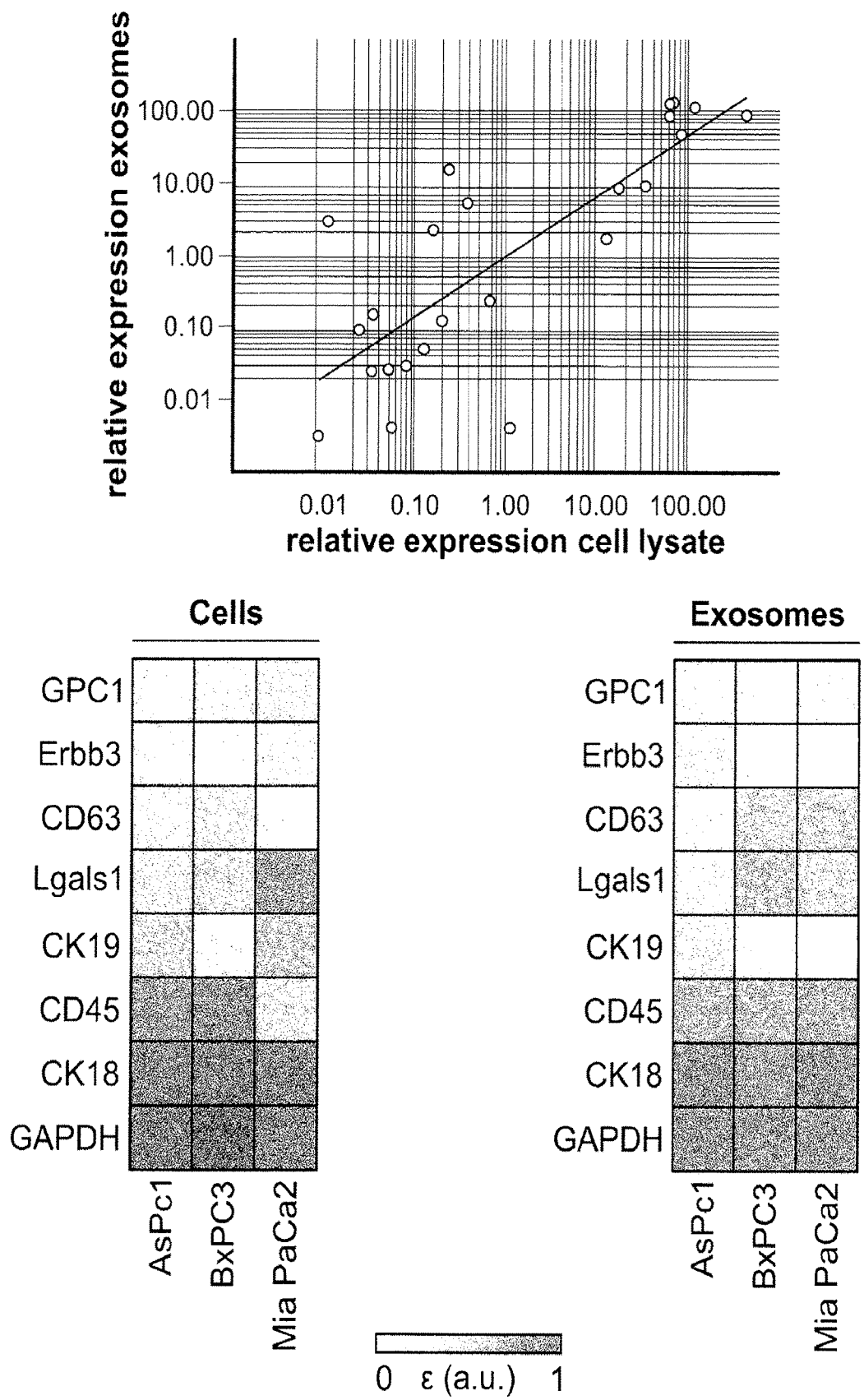
FIG. 18 shows the correlation between cells and exosomes.
Figure 19:
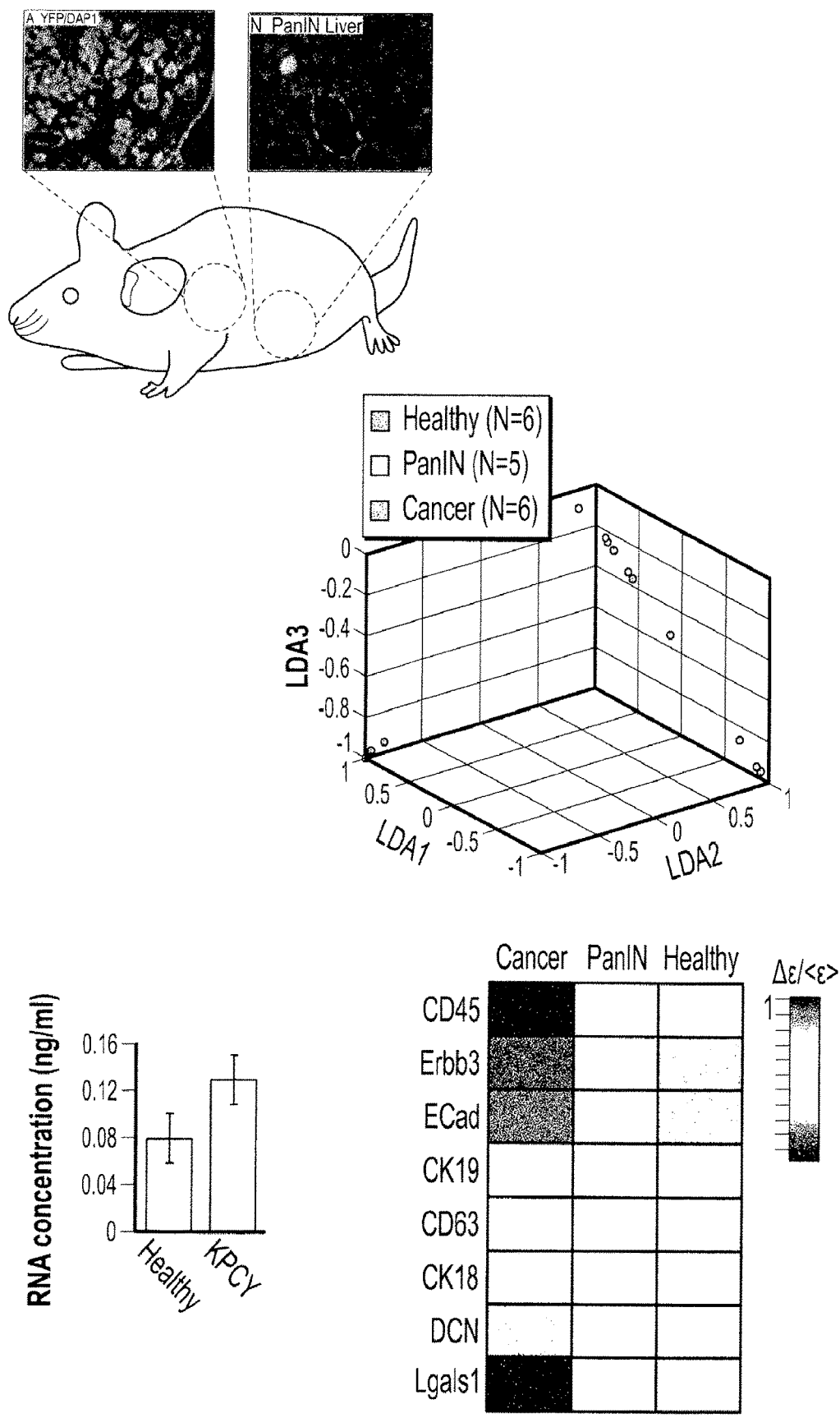
FIG. 19 shows a graph demonstrating the ability to distinguish healthy mice from pre-cancer mice using a magnetic separation filter in accordance with the present invention.

FIG. 17 shows the process used to isolate the RNA from exosomes. Serum was magnetically labeled with anti-biotin magnetic nanoparticles and isolated using a TEMPO filter according to an embodiment of the present invention. The RNA was extracted from the exosomes and amplified using qPCR. The cells and exosomes are positively correlated (see FIG. 18) and it was possible to distinguish pre-cancer mice from healthy mice (see FIG. 19).

Characterization and Validation of Exosome Isolation Using ExoTENPO

Figure 22A:
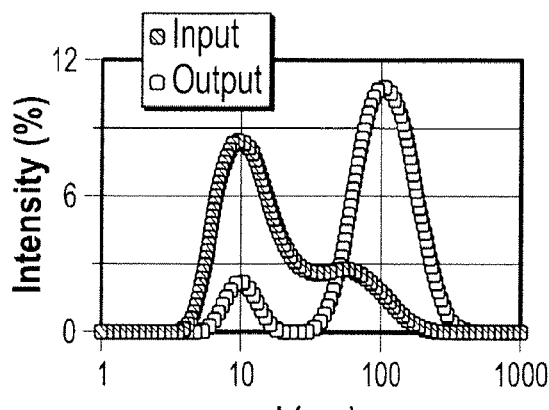
FIG. 22a shows the size distribution of exosomes isolated using an ExoTENPO from a human cell line (MiaPaCa2), measured using dynamic light scattering (DLS) according to one embodiment. The input (orange), cell culture media, consisted of primarily debris (d=14.11 nm). Whereas the exosomes isolated on ExoTENPO consisted primarily of exosomes (d=77 nm).
Figure 22B:
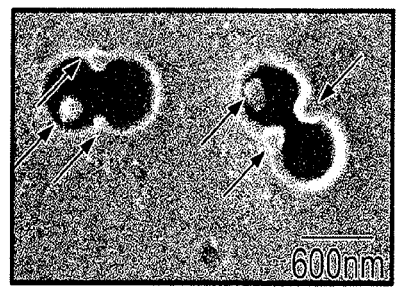
FIG. 22b shows a scanning electron microscopy (SEM) image of exosomes captured at the edge of the ExoTENPO pores according to one embodiment.

Next, the capability of our chip to isolate exosomes was tested using exosomes derived from a human pancreatic cancer cell line. Exosomes were labeled in media from MiaPaCa2 cells with 50 nm iron oxide magnetic nanoparticles (Miltenyi Biotec) using a cocktail of the pan-exosome markers, CD81, CD9, and CD63. A two-step magnetic labeling process was used, wherein the exosomes were first incubated with the cocktail of biotinylated antibodies and subsequently incubated with anti-biotin MNPs. All testing was carried out at a volumetric flow rate of $\varphi=10$ mL/hr. To validate that the ExoTENPO filter was capturing exosomes, the input and the output using dynamic light scattering (DLS) was measured. In the unprocessed cell culture media there was a distinct peak at $d=50.7$ nm, consistent with the size of exosomes and a larger population of smaller particles $d=10.1$ nm that were likely debris (FIG. 22a). The exosomes captured by the device were analyzed by eluting the exosomes captured oo the ExoTENPO for off-chip analysis. Measuring this elution using DLS, it was found that the majority of particles (90% purity) captured by the chip were $d=105.7$ nm, consistent with that of exosomes. (FIG. 22a) Moreover, the exosomes were also fixed directly on the ExoTENPO nanopores after capture, and imaged using scanning electron microscopy (SEM) (University of Pennsylvania School of Medicine, Electron Microscopy Resource Laboratory) (FIG. 22b). Objects were observed with a morphology consistent with exosomes.

Isolation of DNA and RNA Cargo from Exosomes

Figure 22C:
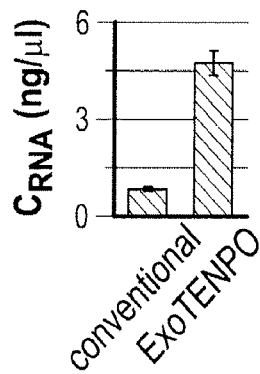
FIG. 22c shows the RNA yield (ng/μl) from an in-vivo murine model achieved by ExoTENPO according to one embodiment compared to that achieved by conventional methods (N=5 for conventional, N=10 for the chip).
Figure 22D:
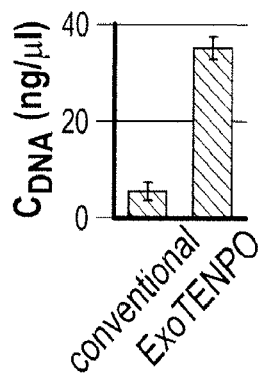
FIG. 22d shows DNA yield (ng/μl) from a murine model compared between ExoTENPO according to one embodiment and conventional methods (N=3 for conventional, N=3 for the chip).
Figure 22F:
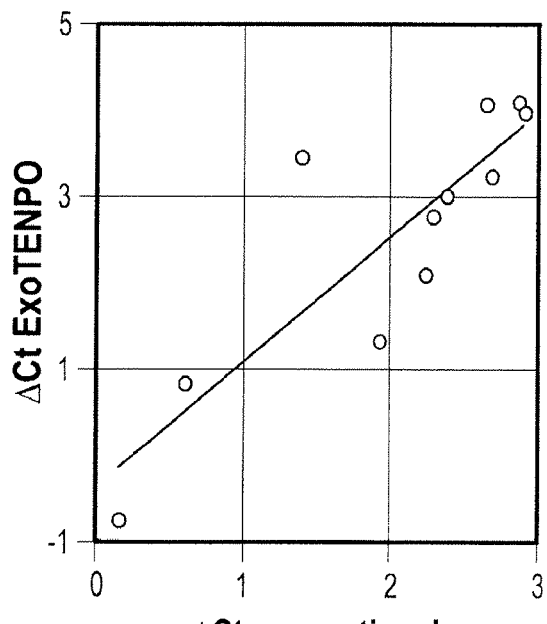
FIG. 22f shows the measured PCR threshold cycle $C_t$, of exosomal RNA isolated using ExoTENPO according to one embodiment and conventional methods plotted versus one another and showing excellent linear correlation ($R^2$=0.8).
Figure 22E:
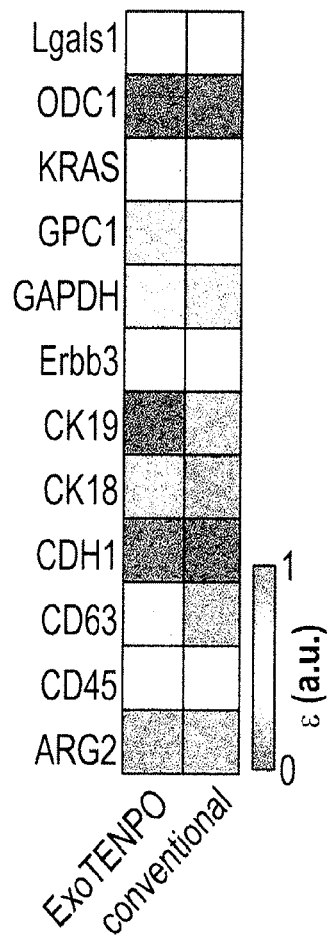
FIG. 22e shows the relative RNA expression level of 12 genes compared between ExoTENPO according to one embodiment and conventional methods using a human cell line culture media (MiaPaCa2) and shows the measured PCR threshold cycle $C_t$, of exosomal RNA isolated using ExoTENPO according to one embodiment and conventional methods as a heat map.
Figure 27A:
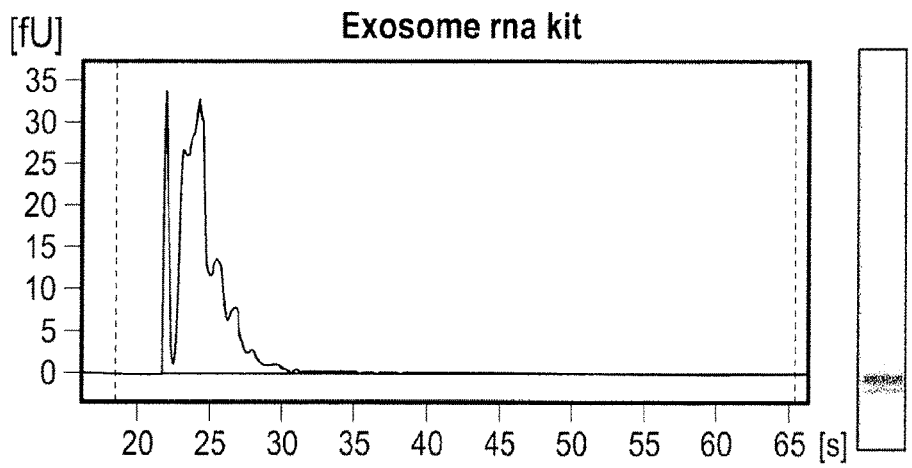
FIGS. 27a and 27b show bioanalyzer data that shows size distribution of total exosomal RNAs from mice using the conventional method (FIG. 27a) and a chip according to one embodiment (FIG. 27b).
Figure 27B:
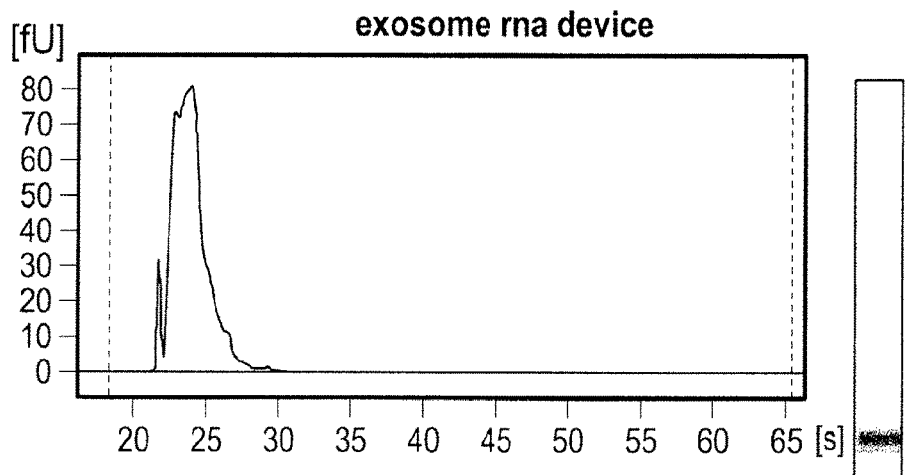
Figure 27C:
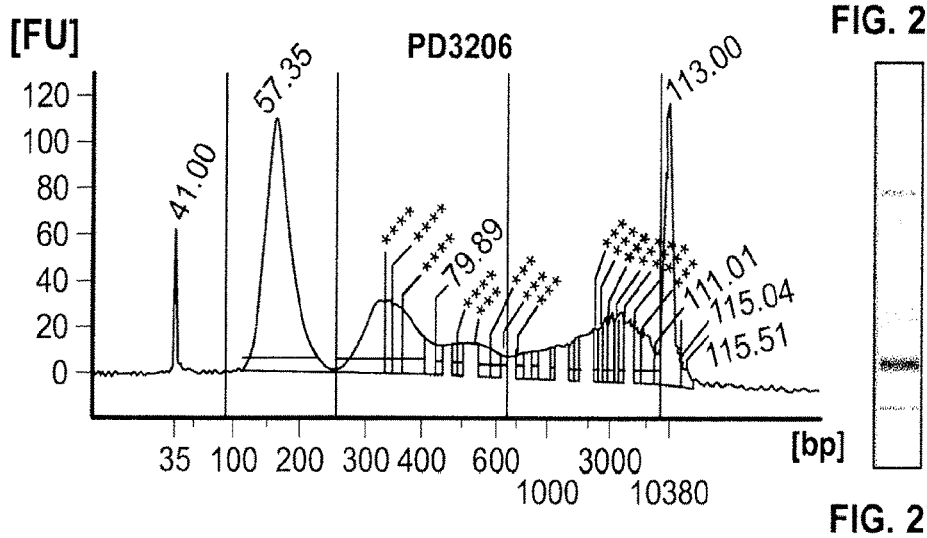
FIG. 27c shows bioanalyzer data of exosomal DNAs from KPCY mouse.
Figure 28A:
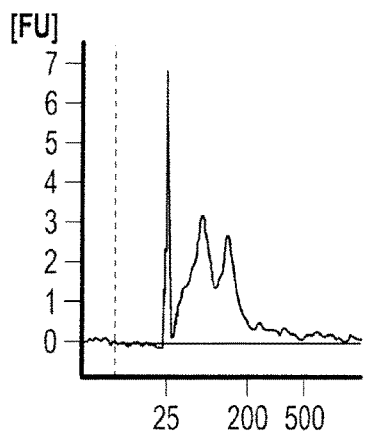
FIGS. 28a and 28b show bioanalyzer data that shows size distribution of total exosomal RNAs from human using a chip according to one embodiment (FIG. 28a) and the conventional method (FIG. 28b).
Figure 28B:
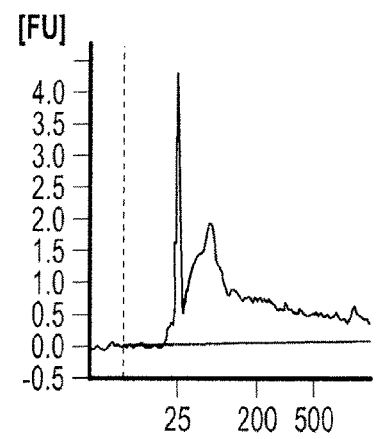
Figure 28C:
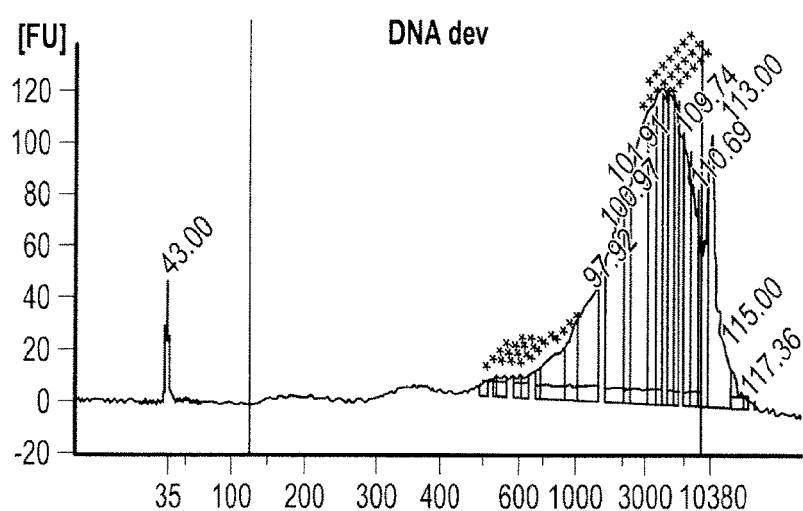
FIGS. 28c and 28d show bioanalyzer data of exosomal DNAs from human using a chip according to one embodiment (FIG. 28c) and the conventional method (FIG. 28d).
Figure 28D:
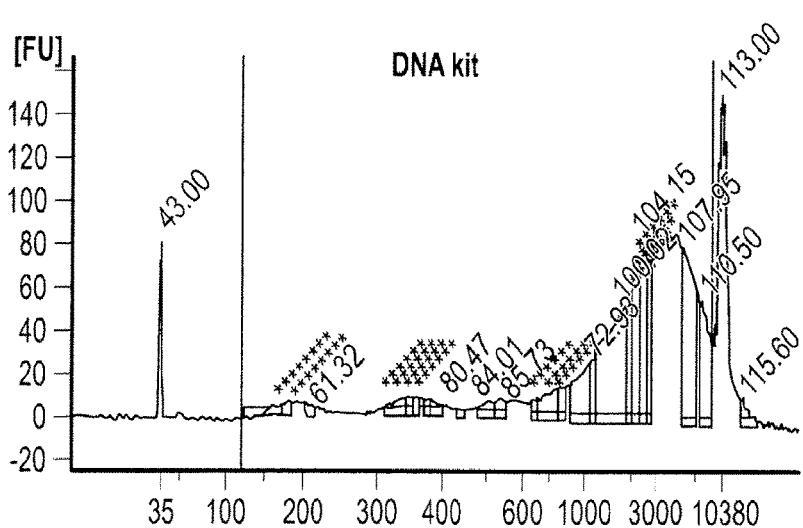

The extraction of nucleic cargos (RNA, DNA) was integrated on the ExoTENPO filter for downstream analysis. To do this, the exosomes were first lysed and the nucleic acids extracted (Total Exosomal RNA Isolation Kit, Life Technologies). The chip's extraction of nucleic acid were compared to the yield of a conventional centrifugal technique (Total Exosome Isolation Kit, Life Technologies). A 6× improvement was achieved in the quantity of both RNA and DNA recovered from mice plasma (FIG. 22c, d). The size and quality of the exosomal RNA and DNA extracted from mice plasma were characterized using a Bioanalyzer. From both the conventional method and the ExoTENPO chip, exosomal RNAs had the greatest occurrence at 24 bp, with a range from 22-30 bp for exosomes from a KPCY mouse and 25-200 bp for exosomes from a human cell line (AsPC1) (FIG. 27). For exosomes captured using the conventional size-based method, there were a greater abundance of smaller (<20 bp) exosomal RNAs, suggesting that the conventional method lead to more degraded RNA (FIG. 27). Exosomal DNA isolated using the ExoTENPO chip was also analyzed, finding DNA in the range of 35 bp to 10 kbp (FIG. S2). It was not possible to compare the exosomal DNA capture between our chip and the conventional method, as the conventional method did not yield a sufficient quantity of material with 3 mL of plasma. Next, it was validated that the relative quantities of exosomal mRNA measured in exosomes isolated using the ExoTENPO matched that of the isolate acquired using a conventional method (Total Exosome Isolation Kit, Life Technologies). Twelve different genes were quantified using qPCR and their mRNA expression levels were measured (FIG. 22e), and a positive correlation ($R^2=0.80$) was found between the relative abundance of RNA isolated using ExoTENPO and a conventional size-based method (FIG. 22f). Thus, the ExoTENPO chip enabled the efficient isolation of exosomes, whose RNA profile closely resembles that of the conventionally isolated material.

Comparison of mRNA Content of Exosomes Versus Cells

One embodiment of the ExoTENPO filter is to monitor the state of difficult to access tumor cells by measuring the more easily accessible circulating exosomes. To validate this approach, the mRNA content of exosomes isolated using the ExoTENPO chip was compared with the mRNA expression of their cells of origin and a strong correlation was found. The mRNA expression was measured using qPCR in both the cellular lysate (FIG. 23a) and in the exosome isolate (FIG. 23b) for 5 different human pancreatic cancer cell lines and 6 different genes relevant to pancreatic cancer in duplicate. mRNA expression in this analysis was normalized to the mean expression for each sample. The RNA expression levels from exosomes and cells were positively correlated ($R^2=0.87$), but it was observed that certain mRNA were packaged reproducibly into exosomes more (e.g. Erbb3) or less (e.g. CK18) than others (FIG. 23c). Relative expression of mRNA varied by as much as 2 orders of magnitude between the cell lysate and exosome isolate. Thus, it was observed that while the exosomal cargo is a reflection of the cells from which the exosomes originate, certain mRNA species are packaged into exosomes at rates that are reproducibly higher or lower than other mRNAs.

Enrichment of Specific Exosome Populations from Complex Media

One advantage of the ExoTENPO filter according to an embodiment of the present disclosure is that it can positively capture specific sub-populations of exosomes based on the modular selection of the affinity ligand(s) during magnetic labeling, enabling improved specificity of exosomal diagnostics. In addition to diagnostics, specific capture may result in high purity enriched population of interest, which can be used to aid in the study the biological function of exosomes. To analyze the role of capturing specific exosome sub-populations for cancer diagnostics, the ability to isolate tumor derived exosomes from serum comparing pan exosome markers to an epithelial specific marker was determined. A model system was used, which consisted of 15 ml of PD6910 media spiked into 1 ml of healthy mouse plasma. From this model system exosomes were isolated using a cocktail of pan exosome markers (CD63, CD9, CD81) as well as a tumor-specific marker (EpCAM) that is known to be expressed by cancer cells. Compared to pan exosome marker based capture, capture using EpCAM showed a greater difference in mRNA expression level $\varepsilon=C_{t,spiked}-C_{t,healthy}$ between plasma samples spiked with tumor derived exosomes $C_{t,spiked}$ and a negative control of only healthy plasma $C_{t,healthy}$ (FIG. 24a) By using DLS, it was confirmed that EpCAM captured particles had a diameter $d=105.7$ nm (FIG. 24b). Thus, it was observed that EpCAM capture could more specifically isolate tumor derived exosomes from plasma than pan exosome capture, and the particles isolated using EpCAM have a diameter consistent with that of exosomes.

Early Diagnosis of Pancreatic Cancer Using Exosomal RNA and DNA

Pancreatic cancer currently has a five year survival rate of only 8% due to the presence of metastatic disease in the majority of patients at diagnosis. Better tools to detect the disease early and to guide treatment more effectively may improve outcomes for this devastating disease. To explore the performance of the ExoTENPO for the early detection of pancreatic cancer, a study on a cohort of KPCY mice was studied. These mice were genetically engineered to develop pancreatic cancers that faithfully reproduce the human disease (FIG. 24c). Moreover, cancer cells in the KPCY mice express yellow fluorescent protein (YFP), enabling the staging of the cancer, even at pre-cancerous stages. With such properties, these mice are ideally suited to evaluate the ExoTENPO chip's capability to detect disease at different stages of disease.

The exosomal mRNA signatures of mice that were healthy, mice with pre-cancerous lesions (PanIN), and mice with cancer were measured, and from these measurements a predictive panel of exosome-based biomarkers for pancreatic cancer was developed and tested using an independent, user blinded cohort of mice. A panel of 9 candidate exosomal mRNA biomarkers using qPCR that are known to be differentially expressed in both tumor cells and circulating tumor cells relative to healthy cells was selected. Based on the results of the assay optimization experiments (FIG. 24a), exosomes were isolated from approximately 0.5 mL of plasma from each mice using EpCAM isolation on the ExoTENPO. The exosomal mRNA profile was measured using qPCR from a training set of N=6 healthy, N=5 PanIN, and N=6 cancer mice. Amongst these mice, by measuring only the total quantity of mRNA, it was not possible to accurately classify the mice (P>0.5) (FIG. 24d). Amongst the panel of mRNA that was measured, several genes were differentially expressed between the groups (e.g. H3F3A) (FIG. 24e) However, there was no single gene able to classify individual mice into the correct groups, due to the variance in expression amongst mice within groups.

To optimally diagnose the mice, linear discriminant analysis (LDA) was used to identify linear combinations of the mRNA profile that can discriminate mice that are healthy, PanIN, or have cancer. Using the training set data, LDA vectors (LDA_healthy, LDA_PanIN, LDA_cancer) that maximally separate the individual mice into the correct group were generated (FIG. 24f,g). The diagnostic ability of this approach using N−1 cross-validation were first evaluated, wherein one mouse was iteratively removed from the test set and classified using the LDA vectors obtained from the remaining mice. Using this method, every mouse was classified into the correct group (FIG. 24f,g) To further validate this approach, an independent, operator-blinded test set was created that included plasma samples from N=5 healthy, N=5 PanIN, and N=5 cancer mice, and every mouse was classified correctly (FIG. 24h). In addition to mRNA, it was also demonstrated that exosomal DNA could be isolated and analyzed to identify cancer-related mutations (FIG. 24i).

Clinical Diagnostic of Pancreatic Cancer with Exo-TENPO

Figure 25A:
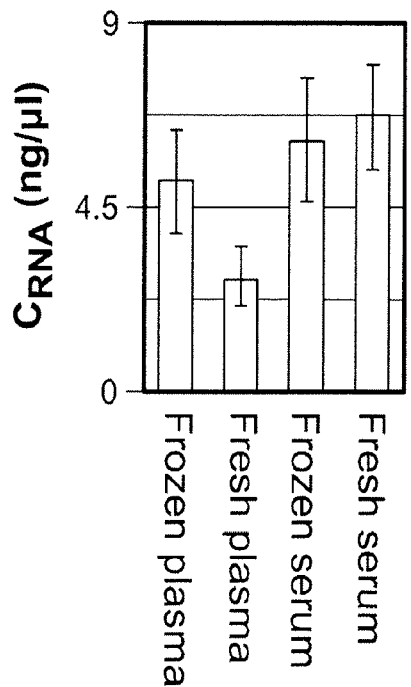
FIG. 25a shows RNA concentration (ng/μl) from different types (serum, plasma) and different conditions (frozen, fresh). Each sample is N=3.
Figure 25B:
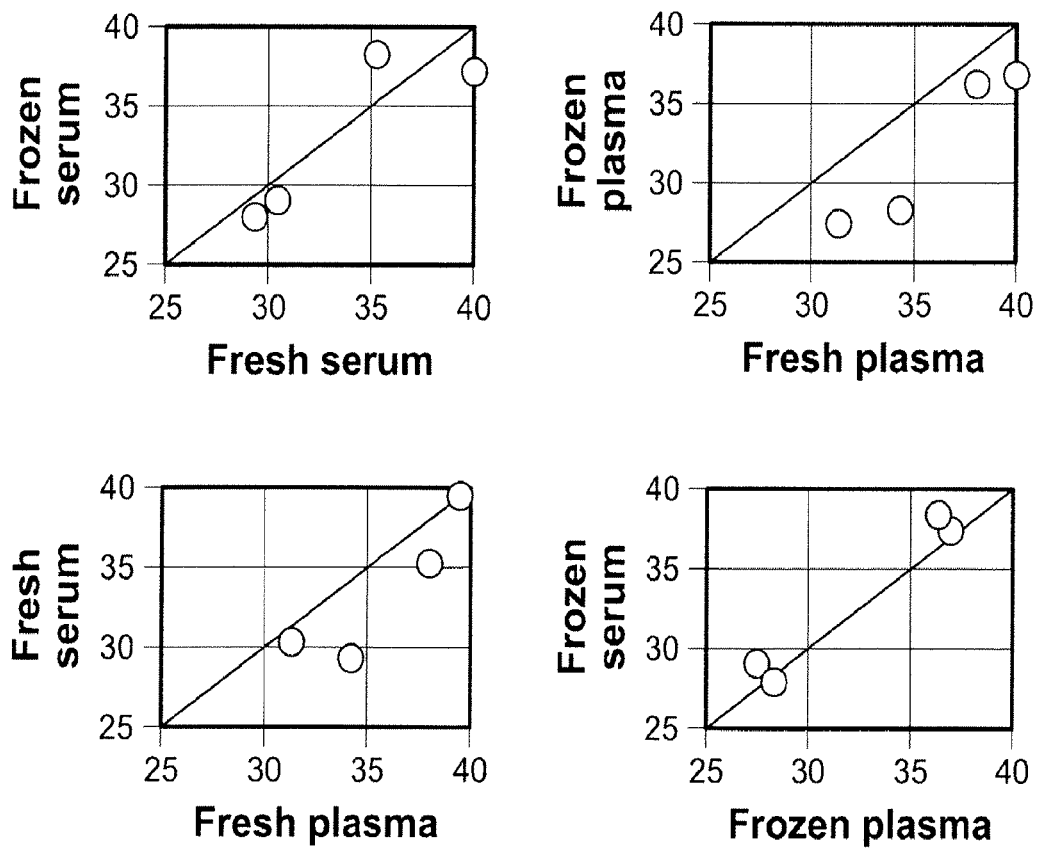
FIG. 25b shows pairwise comparison of different types and different conditions of samples, using $C_t$ values from qPCR.
Figure 25C:
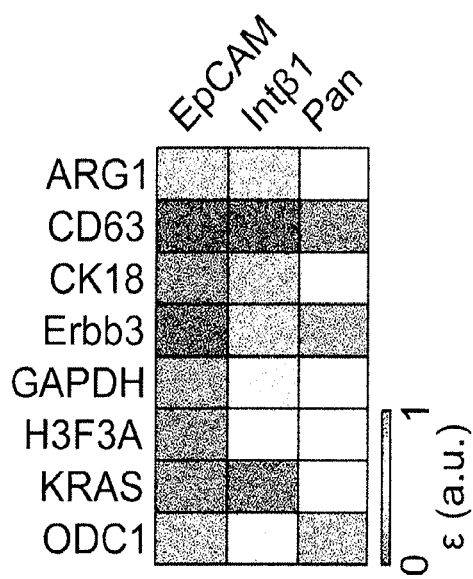
FIG. 25c shows a heat map using four different capture markers (EpCAM, Intb1, Muc1, Pan—CD9, CD63, CD81) to demonstrate the expression level differences of four exosomal mRNA (ARG1, CDH1, KRAS, ODC1) from healthy plasma and healthy plasma spiked with pancreatic cancer cell cultured media (MiaPaCa2).

To evaluate the ExoTENPO's capability to diagnose pancreatic cancer in clinical specimens, the performance of the chip isolating exosomes from human blood samples was characterized. The recovery of exosomal RNA and DNA using the ExoTENPO in healthy human plasma samples, using pan exosome isolation (CD63, CD9, CD81) was first compared to a conventional ultracentrifugal method (Total Exosome Isolation Kit, Life Technologies) and found a 1.6× improvement in recovery (FIG. 29). To optimize the ExoTENPO for practical clinical use, the recovery of exosomal RNA was compared in a variety of common clinical sample types, including fresh plasma, fresh serum, frozen plasma, and frozen serum using pan exosome isolation. It was found that there was not a significant difference in the RNA recovery from the various sample types (FIG. 25a) Next, pairwise comparisons of the relative abundance of mRNA targets (CK18, CD63, Erbb3, KRAS) was performed and it was found that similar exosomal RNA cargo profiles ($R^2 > 0.77$) were obtained from the different sample preparations (FIG. 25b). Thus, it was concluded that the Exo-TENPO platform can be used on any of these available sample types and provide comparable information. To identify the affinity ligand to use for the clinical measurements, the ability to specifically isolate tumor derived exosomes from serum using pan exosome isolation versus cancer epitopes was compared. A model system, which consisted of 12 ml of media from a cultured pancreatic cancer cell line (BxPC3) spiked into 3 ml of healthy human plasma was used. From this model system exosomes were isolated using a cocktail of pan exosome markers (CD63, CD9, CD81) as well as a tumor-specific markers, including EpCAM and Intβ1. Compared to pan exosome marker based capture, positive capture using EpCAM showed the greatest mRNA expression level difference $\varepsilon = C_{t,spiked} - C_{t,healthy}$ between cancer exosome spiked plasma $C_{t,spiked}$ and healthy plasma $C_{t,healthy}$ (FIG. 25c).

Figure 25D:
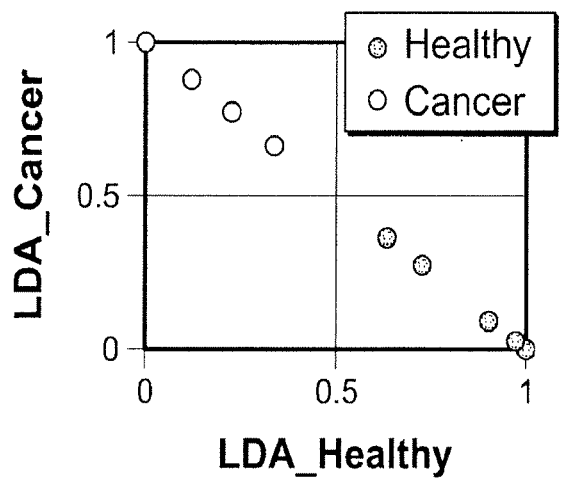
FIG. 25d shows linear discriminant analysis (LDA) vectors algorithmically generated based on the RNA expression levels to separate healthy (green) from cancer patients (orange).
Figure 25E:
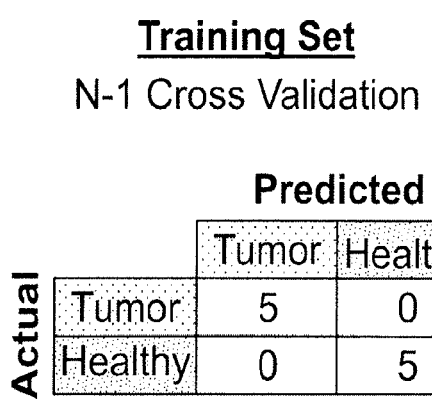
FIG. 25e shows a confusion matrix demonstrating the capability to discriminate healthy versus cancer using N−1 cross-validation of the training set, and achieving perfect discrimination.
Figure 25F:
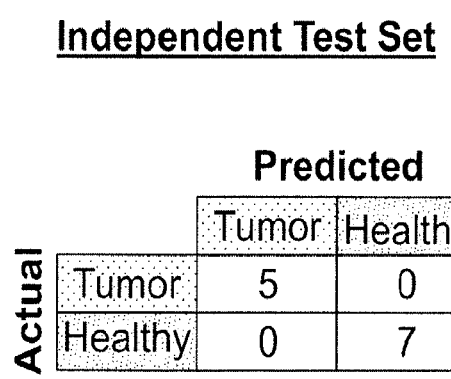
FIG. 25f shows a confusion matrix summarizing an independent, user blinded test set achieving perfect discrimination of patients with cancer vs. patients that are healthy.

To explore the performance of the ExoTENPO for cancer diagnostics in patient-derived specimens, a study was conducted on a cohort of patients (N=10) with advanced pancreatic cancer. As a negative control, N=12 age matched healthy patients were included. The exosomal mRNA signature of patients that were healthy and patients that had cancer were measured, and from these measurements a predictive panel of exosome-based biomarkers for pancreatic cancer was developed and tested using an independent, user blinded cohort of patients. The same panel of 9 candidate exosomal mRNA biomarkers identified using our mouse measurements was used. Exosomes were isolated from approximately 3 mL of plasma from each patient using EpCAM based isolation on the ExoTENPO. The exosomal mRNA profile was measured from a training set of N=5 healthy controls and N=5 patients with cancer. Amongst the panel of mRNA that were measured, several genes were differentially expressed between the groups (e.g. CD63). No single gene was able to classify individual patients into the correct groups due to the variance in expression amongst patients within groups. Therefore, using the training set data, LDA vectors (LDA_healthy, LDA_cancer) were generated that maximally separated the patients into the correct group (FIG. 25d). The diagnostic ability of this approach was first evaluated using N−1 cross-validation, and every patient was classified into the correct group. (FIG. 25e) To further validate this approach, an independent, operator-blinded test set was created that included plasma samples from N=7 healthy controls and N=5 patients with cancer, and every patient was classified correctly. (FIG. 25f)

Traumatic Brain Injury Diagnostics Using ExoTENPO

Traumatic brain injury (TBI) occurs in approximately 2.5 million people each year. Although it is a very common worldwide incident, the lack of molecular marker based diagnostic tools complicates clinical decision for monitoring and treatment of patients. An accurate assessment of the incident is crucial especially when the TBI patients sustain a secondary injury that can lead to a long-term physical, emotional, and behavioral disability. For diagnostics, imaging technologies such as computerized tomography (CT) scans and magnetic resonance imaging (MRI) can be used for severe TBI, but mild TBI (mTBI) diagnostics, which comprise of 70-90% of the TBI cases, are currently limited to patient reports and clinical symptoms, which do not provide an objective assessment.

Therefore, there is a great need for molecular biomarkers that can help guide monitoring and treatment of mTBI patients. There have been studies on biomarker discovery for mTBI, but the approach is mostly hypothesis-driven, screening for TBI pathophysiology associated biofluid markers. Exosomes have gained a great attention as a potential biomarker for liquid biopsy. As exosomes are circulating nano vesicles (30-200 nm) that have molecular information (mRNA, miRNA, DNA, and protein) of their mother cells, an open-ended approach is possible. For example, the list of proteins and nucleic acids can be obtained using mass spectrometry and sequencing technologies. This enables an unbiased biomarker discovery for multiple diseases. Conventionally, exosomes are isolated using a bulky ultracentrifuge, which causes high loss, low purity, and long assay time. Due to these limitations, downstream analysis of exosomes is not practical and extremely difficult to achieve a reliable, meaningful result. To address these challenges, small RNA sequencing on exosomes isolated using an ExoTENPO chip according to an embodiment of the present disclosure. The ExoTENPO chip achieved >5× yield, high purity (90%), and extremely rapid (>10 ml/hr) assay time. This experiment focused on discovering brain-derived exosomal miRNAs that were differentially expressed after mTBI using blast-induced injured mice. The ExoTENPO chip was used to isolate exosomes based on their glutamate receptor ½ (GluR1/2) expression to profile brain-derived exosomes. It was discovered that exosomal miRNAs were differentially expressed after mTBI. A subset of these exosomal miRNAs were use to diagnose mTBI mice, achieving 100% sensitivity and 100% specificity.

Brain-derived were first isolated using an ExoTENPO chip having a pore diameter d=600 nm (FIG. 31a). Exosomes of interest were magnetically labeled using biotinylated antibody and anti-biotin magnetic microbead complex. As shown in the finite element simulation magnetic field plot (FIG. 31b), the edge of the pores had the strongest magnetic field gradient, where the exosomes are attracted and captured. To prove that exosomes were captured based on their sizes, cortical neuron cultured media (input) was run through the chip and the eluted sample (isolate) was measured using dynamic light scattering (DLS). The input showed a major peak at 8.72 nm, which was considered to be small debris. The isolate from the ExoTENPO chip showed a major peak at 141.8 nm, which was in the range of exosome size (30-200 nm) (FIG. 31c). Scanning electron microscopy (SEM) was also performed in order to show that exosomes were captured at the edge of the pores of the chip. It was observed that 150-200 nm exosomes were captured at the edge of the pores (FIG. 31d). After validation of exosome capture using cell cultured media, mouse plasma was used for biomarker discovery. First, mouse plasma was run through the ExoTENPO chip (FIG. 31e). The chip allowed for specific enrichment of brain-derived exosomes by targeting the exosomes using an anti-glutamate receptor ½ (GluR2) antibody (biotin). The biotinylated antibody was incubated with anti-biotin microbeads, which were magnetic iron oxide nanoparticles. As the plasma flowed through the chip, the labeled brain-derived exosomes were captured on edge of the pores of the chip. After exosome capture, the total exosomal RNA was isolated by lysing on the chip. Then, a small RNA library prep set (BioLabs) was used for RNA sequencing. Using the prepared samples, an RNA sequencer (Illumina) was run and the RNA sequencing data was evaluated using quantitative polymerase chain reaction (qPCR).

RNA sequencing data showed that 565 miRNAs were expressed by brain-derived exosomes from mice. Exosomal miRNAs were sequenced from two groups, control and injured mice. Healthy mice without injury were used as a control, and blast-induced injury was performed to mimic mTBI.

Figure 32A:
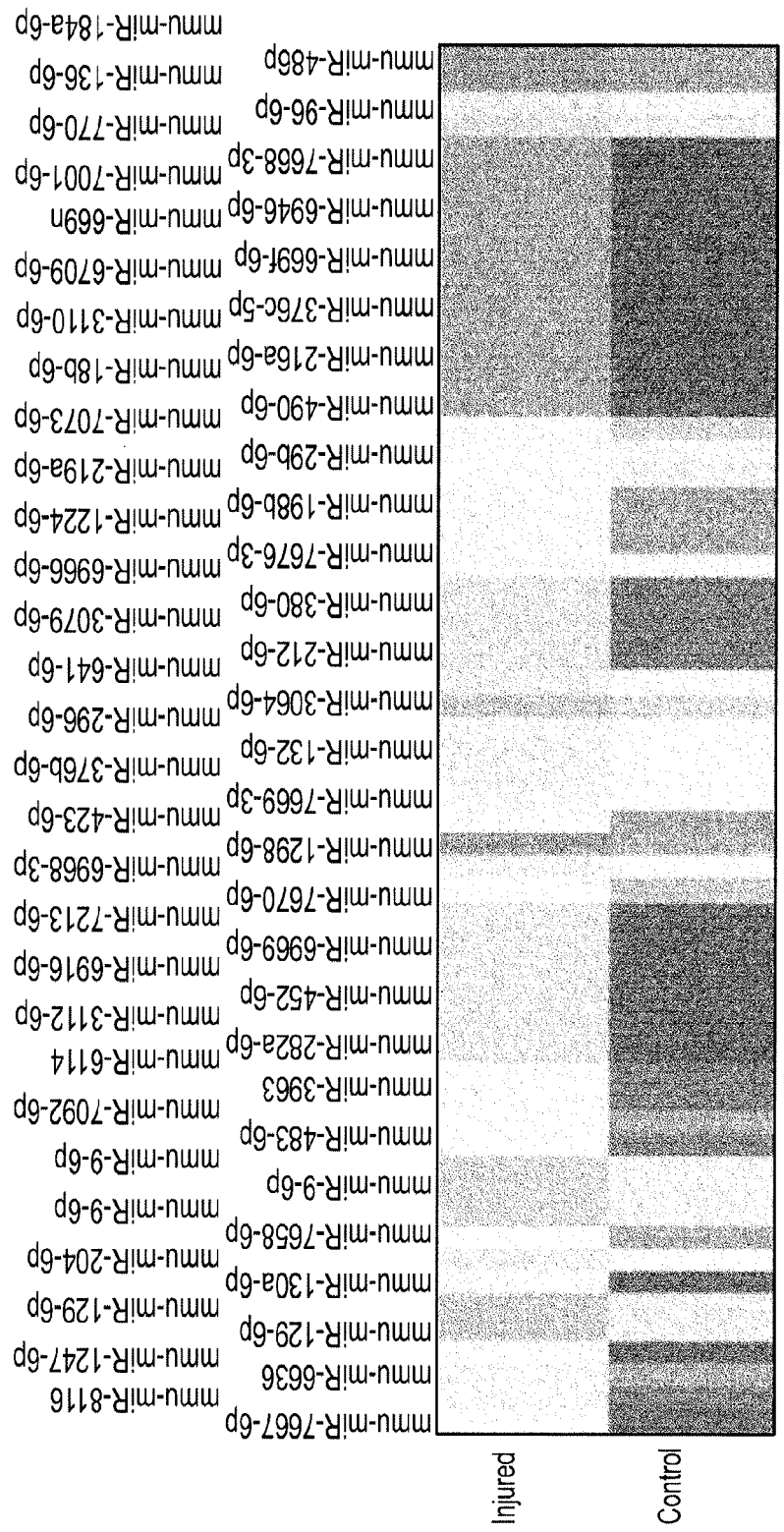
FIG. 32A shows a heat map of the expression level of 128 miRNAs from a control group and an injured group.
Figure 32A:
Figure 32B:
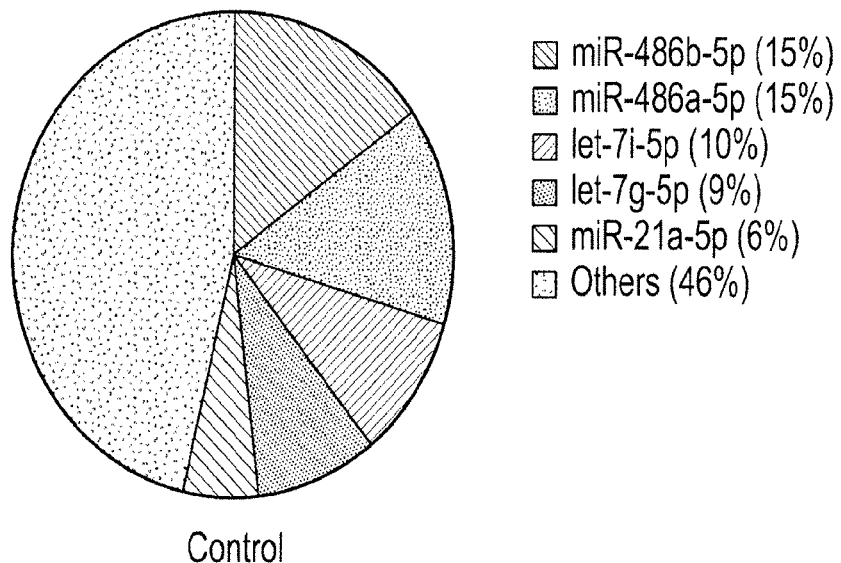
FIGS. 32B and 32C show the relative levels for the most abundant miRNAs from a control group and an injured group, respectively.
Figure 32C:
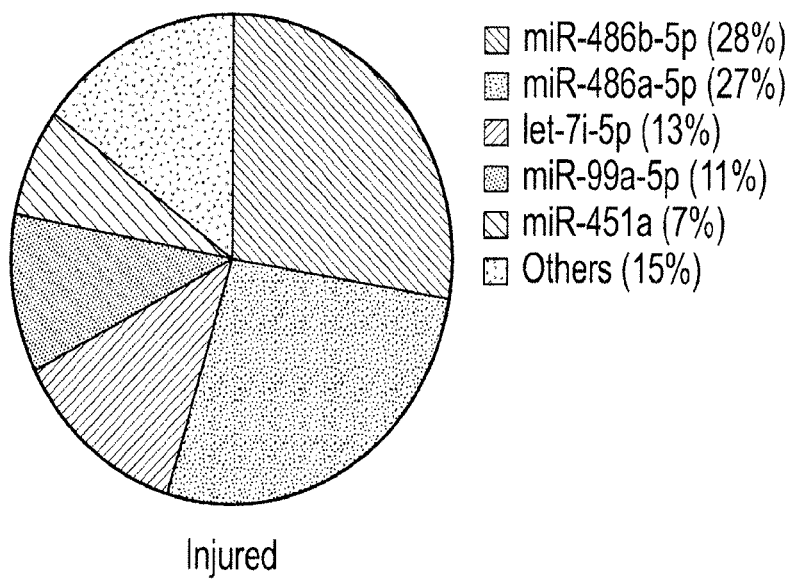

Among 565 express miRNAs, there were 128 miRNAs that had raw counts more than 50. The expression level of the 128 miRNAs from both groups (control, injured) is shown as a heat map (FIG. 32a). As expected, there were some miRNAs that were differentially expressed from the two groups and some that were similar to each other. The composition of brain-derived exosomal miRNAs expressed by control mice and those expressed by injured mice was also observed. The top 3 most abundant miRNAs were the same (miR-486b-5p, miR-486a-5p, let-7i-5p) between two the groups.

However, brain-derived exosomes from injured mice showed a greater percentage for miR-486a/b-5p while let-7i-5p was not that different. Kyoto encyclopedia of genes and genomes (KEGG) pathway analysis was performed to find a statistically significant pathways that are related to brain. Here, 8 different pathways were found with related miRNAs and their target genes, as shown in Table 1.

TABLE 1

| KEGG pathway | p-value | #genes | #miRNAs |
| --- | --- | --- | --- |
| Axon guidance | 6.33E−08 | 69 | 39 |
| Long-term potentiation | 5.89E−05 | 39 | 29 |
| Glutamatergic synapse | 5.89E−05 | 54 | 34 |
| Oxytocin signaling pathway | 6.71E−05 | 77 | 39 |
| GABAergic synapse | 0.001291407 | 34 | 27 |
| Dopaminergic synapse | 0.001778928 | 60 | 30 |
| Neurotrophin signaling pathway | 0.001809901 | 57 | 33 |
| Cholinergic synapse | 0.03748049 | 51 | 31 |

Figure 33A:
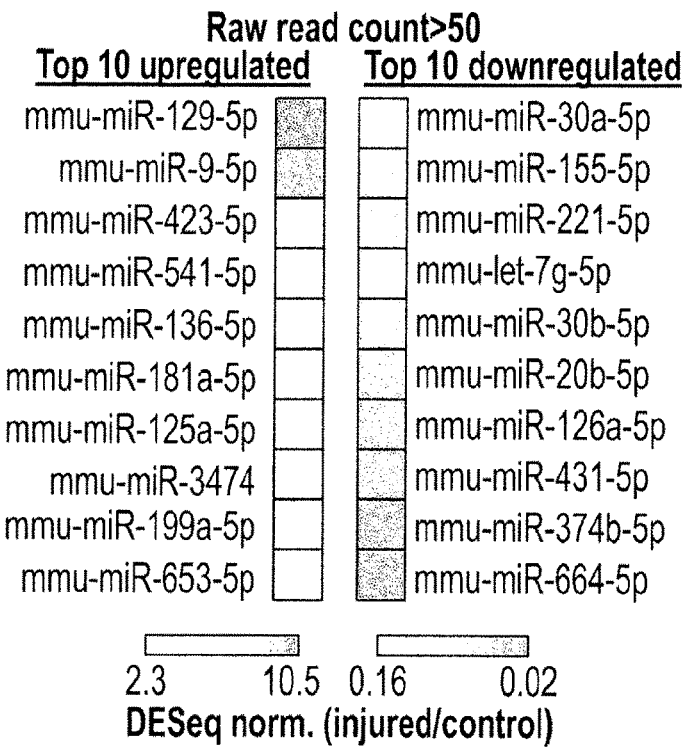
FIG. 33A shows the top 10 upregulated and downregulated brain-derived exosomal miRNAs that had more than 50 raw read counts examined.
Figure 33B:
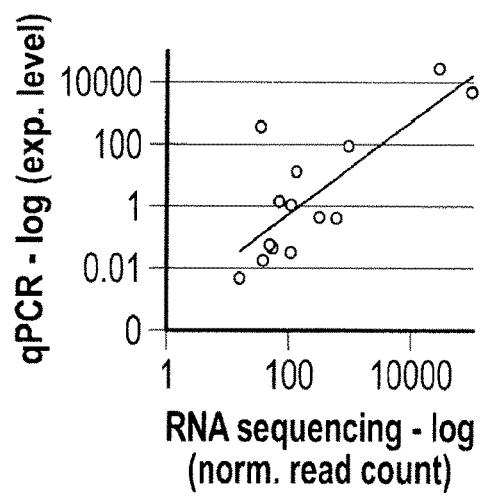
FIG. 33B shows the correlation between the expression level from qPCR and the normalized read count from RNA sequencing.
Figure 33C:
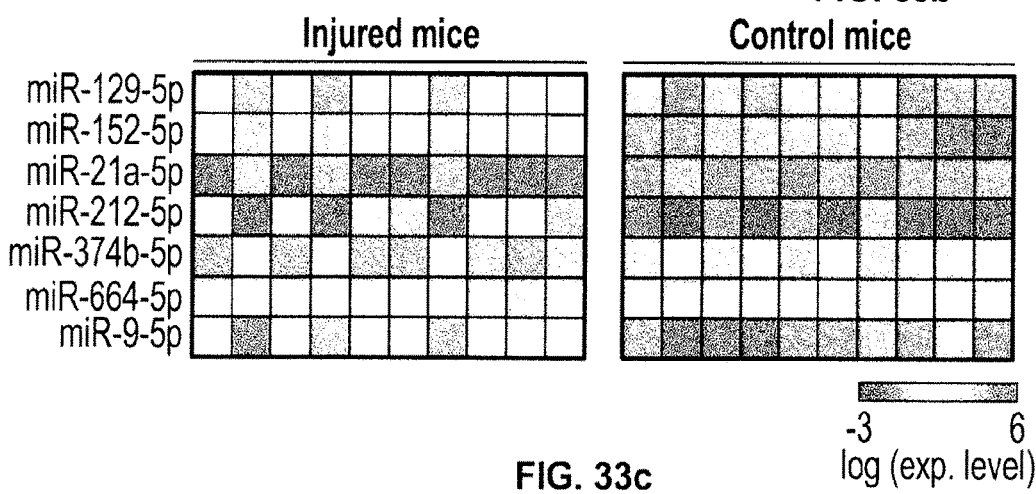
FIG. 33C shows heat maps of the expression level of the selected miRNA panel from the injured group and the control group.

The raw read counts from both control and injured groups were normalized using DESeq. Then, the ratio of injured to control DESeq normalized values was observed. For biomarker selection, top 10 upregulated and downregulated brain-derived exosomal miRNAs that had more than 50 raw read counts were examined (FIG. 33a). From the list, 2 upregulated miRNAs (miR-129-5p, miR-9-5p) and 2 downregulated miRNAs (miR-374b-5p, miR-664-3p) were selected to validate using qPCR. miR-212-5p was chosen as a potential to be a reference due to similar DESeq normalized values from both control and injured groups. miR-21a-5p was chosen as the last marker based on the findings that showed it alleviates secondary blood-brain barrier damage after TBI and apoptosis of cortical neurons. Using qPCR, expression level of individual miRNA markers was obtained. There was a positive correlation between the expression level from qPCR and the normalized read count from RNA sequencing, with some variance (FIG. 33b). Then, heat maps were generated to observe a pattern for the expression level of the selected miRNA panel from different groups (injured, control) (FIG. 33c). The patterns were different, but there were no miRNAs that were upregulated or downregulated in each individual mouse from one group.

mTBI diagnosis was performed on mice using the panel of miRNA markers that were validated using qPCR. Using the whole panel of miRNA markers, we were able to achieve 100% sensitivity and 100% specificity (FIG. 34a). In order to analyze the pattern for diagnosis, linear discriminant analysis (LDA) was used.

NEBNext Small RNA Library Prep Set for Illumina (BioLabs) was used to make a library. RNA was isolated on chip using Total Exosomal RNA Isolation Kit (Life Technologies).

Then, the RNA amount was measured using Qubit (Life Technologies) and as recommended by the protocol, the samples with more than 100 ng of RNA were selected for usage. Then, quality control check was performed on a BioAnalyzer using a DNA 1000 chip. For size selection, AMPure XP beads were used (Beckman Coulter). 140-150 bp sizes were selected using the beads and the sizes were confirmed by the BioAnalyzer using High Sensitivity Chip. A NextSeq 500/550 kit (FC-404-2005, Illumina) was used for RNA sequencing.

Sample Collection (Mice)

All mouse work was performed in compliance with institutional and IACUC guidelines. Blood was obtained by cardiac puncture from the right ventricle of tumor-bearing KPCY mice and collected in sodium citrate coated blood collection tubes (BD Vacutainer™). Plasma was isolated by centrifuging the blood at 1600 g for 10 min, followed by a second spin at 3000 g for 10 min to remove cellular contamination.

Sample Collection (Human)

Peripheral whole blood was obtained from PDA patients with advanced pancreatic cancer and from healthy age- and gender-matched controls at the University of Pennsylvania Health System. All patients and healthy donors provided written informed consent for blood donation on approved institutional protocols. Whole blood was drawn in either EDTA (Fisher Scientific), Streck Cell-Free DNA BCT® (Streck), or gel serum separation tubes (Fisher Scientific). Plasma and serum were isolated using the following procedures. Within 3 hours of blood draw for EDTA and within 12 hours of blood draw for Streck, tubes were centrifuged at 1600 g for 10 minutes at room temperature with the break off. Next, plasma was transferred to a fresh 15 ml centrifuge tube without disturbing the cellular layer and centrifuged at 3000 g for 10 minutes (EDTA) or 4122 g for 15 minutes (Streck) at room temperature with the break off; this step was repeated with a fresh 15 ml centrifuge tube. After the third spin, plasma was transferred to a fresh 15 ml centrifuge tube, gently mixed, and transferred in 1 ml aliquots to centrifuge tubes and either processed fresh for exosomal RNA or stored immediately at −80° C. for future use. Gel serum separation tubes were stored at room temperature for 30 minutes after blood draw. Within 2 hours of blood draw, serum tubes were centrifuged at 1000 g for 15 minutes at room temperature. Last, serum was transferred in 1 ml aliquots to cryovials and either processed fresh for exosomal RNA or stored immediately at −80° C. for future use.

Cell Culture

Mouse cell lines PD7591, PD483, PD6910 were generated from pancreatic tumor tissue isolated from Pdx1-cre, $Kras^{LSL-G12D}$, $p53^{L+}$, $Rosa^{YFP/YFP}$ (KPCY) mice (Rhim et al Cell 2012). They were cultured in pancreatic ductal epithelium media as previously described (Schreiber, F. S. et al. Successful growth and characterization of mouse pancreatic ductal cells: functional properties of the Ki-RASG12V oncogene. All human cell lines were cultured in media recommended by ATCC.

Exosome Isolation (Kit)

Supernatant fractions from confluent cell cultures (48-72 h) were collected and centrifuged at 1500 rpm for 5 minutes to remove dead cells and debris. Total exosome isolation reagents (from serum, plasma, cell culture media) from Life Technologies were used. The protocol was followed as suggested by the company. Isolated exosomes were stored at 4 C for a short term storage or immediately processed for further analysis.

Exosome Isolation (ExoTENPO)

Anti-biotin ultrapure microbeads (Miltenyi Biotec) and biotinylated antibodies were used for magnetic labeling. For mouse, biotin anti-CD9 antibody (BioLegend) and biotin anti-CD81 antibody (BioLegend) were used. For human, biotin anti-human CD9 antibody (eBioscience), biotin anti-human CD63 antibody (BioLegend), and biotin anti-CD81 antibody (custom made from BioLegend) were used. First, biotinylated antibodies were added to the sample and incubated for 20 mins at room temperature with shaking. Then, anti-biotin ultra pure microbes were added to the samples and incubated for 20 mins at room temperature with shaking. Then the samples were added to the reservoir of the ExoTENPO chip and negative pressure was applied by a programmable syringe pump (Braintree). As the samples were pulled through the chip, magnetically labeled exosomes were captured at the edge of the pores of the chip.

Exosomal RNA Isolation

Total exosome RNA & protein isolation kit (Life Technologies) was used for RNA extraction from isolated exosomes. For the exosomes captured on chip, denaturing solution was added to the chip and the chip was incubated for 5 mins on ice. Then, the lysed solution was taken off chip for acid-phenol separation and washing steps using a spin column. The exosomal RNA was eluted in a small volume (~30 μl) and it was stored at −80 C or processed immediately for further analysis.

Exosomal DNA Isolation

Exosomal DNA was isolated using QUIAamp DNA mini kit (Qiagen). Lysis buffer was directly added on chip and the chip was incubated at 56 C for 10 mins. Then, the lysed solution was taken off chip for the rest of the steps. The exosomal DNA was eluted in a small volume (~30 μl) and it was stored at −20 C or −80 C until usage.

Polymerase Chain Reaction (PCR)

RT-PCR was first performed using exosomal RNA. PrimeScript RT Reagent Kit (Clontech) was used for RT-PCR. Using the kit, the exosomal RNA was mixed with reagents and the sample was in a T100 Thermal Cycler (Bio Rad) followed by the company's protocol.

qPCR

Master mix that consists of SsoAdvanced Universal SYBR Green Supermix (Bio Rad), primers (Integrated DNA Technologies), and water were made at 5:0.5:3.5 ratio and 9 μl of the master mix was added to each well, followed by 1 μl of cDNA. 40 cycles were run with a default setting using CFX384 Touch Real-Time PCR machine (Bio Rad). Triplicates were done for each sample. The melting curves were first checked before the analysis.

Trp53 PCR

The following primers were used to detect the recombined Trp53 allele in exosomal DNA isolated from KPCY mice (F: 5' CACAAAAACAGGTTAAACCCAG 3' R: 5' GAAGACAGAAAAGGGGAGGG 3'). The expected band for the recombined allele is 612 bp.

Linear Discriminant Analysis (LDA)

Using Matlab (R2015b), multiple features (genes) from multiple groups (healthy, PanIN, tumor) were simplified for classification using LDA. The code is shown in FIG. 30. The confusion matrix and the LDA plot were made using results from Matlab. Cross validation (N−1) method was used for data analysis.

NMR Relaxometry 200 nm microbeads (Chemicell) were used to test the enrichment of the chip. Input was made and it was serially diluted to generate a standard curve (T2 relaxation time vs. bead concentration). Then, the input was run through the chip and flow through solution was collected as an output. All the samples were measured using the minispec (Bruker) for T2 relaxation time.

Dynamic Light Scattering (DLS)

In order to get the size distribution of the samples, we used DLS (Zetasizer, Malvern). 300-400 µl of samples was loaded each time and RNA and DNA Measurement The size of the exosomal RNA and DNA was measured using a BioAnalyzer. Exosomal RNA was measured in BioAnalyzer using the Agilent RNA Pico chip at the NAP-Core Facility at the Children's Hospital of Philadelphia. Exosomal DNA was measured in BioAnalyzer using the Agilent High Sensitivity DNA chip at the same facility. The amount and concentration of the exosomal RNA and DNA were measured using the Qubit RNA HS Assay Kit (Thermo Fisher Scientific) and the Qubit ddDNA Assay kit (Thermo Fisher Scientific) respectively.

MagNET Filter

Immunomagnetic sorting is a technique to selectively isolate rare magnetically-tagged cells from heterogeneous suspensions—yet current devices fail to provide high enrichment ($\zeta$) for clinically relevant volumes (>30 mL) and turnaround times (<30 min). Rare cells, such as circulating tumor cells (CTCs), are present in concentrations of $1\text{-}10^2$ in 10 mL of blood, requiring large samples of blood to be processed with high specificity to isolate these cells from the background of $10^5$ leukocytes, $10^{10}$ red blood cells, etc.

Figure 8:
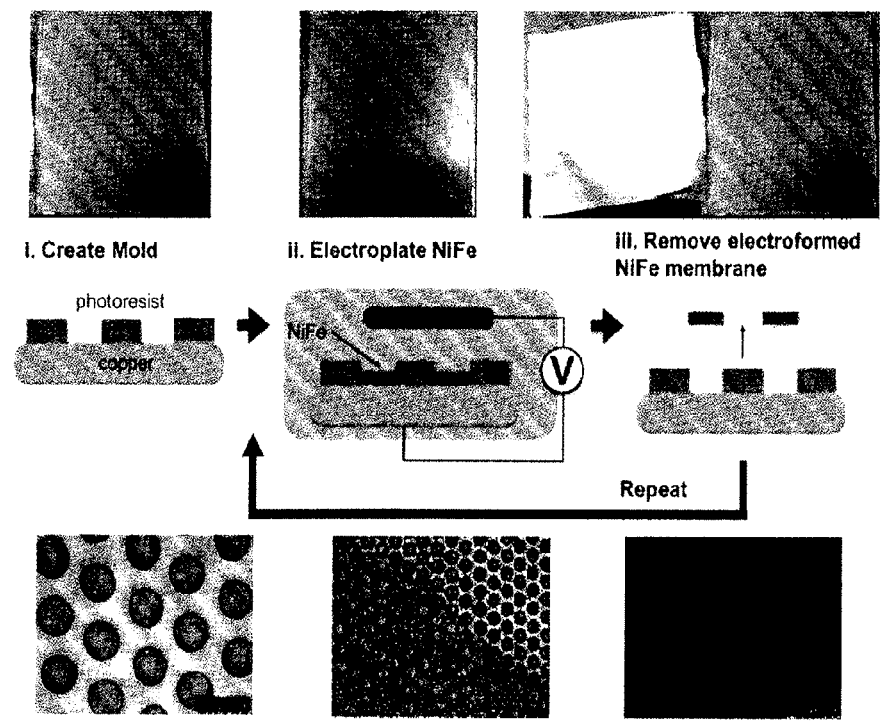
FIG. 8 is a schematic representation showing the method of making a magnetic separation filter according to an embodiment of the present invention.
Figure 9:
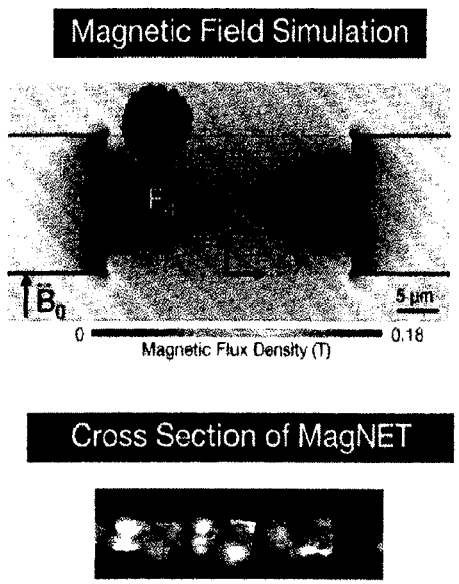
FIG. 9 shows a schematic representation of the magnetic field in the pore of a magnetic separation filter in accordance with an embodiment of the present invention in comparison to a cross section of the filter.
Figure 10:
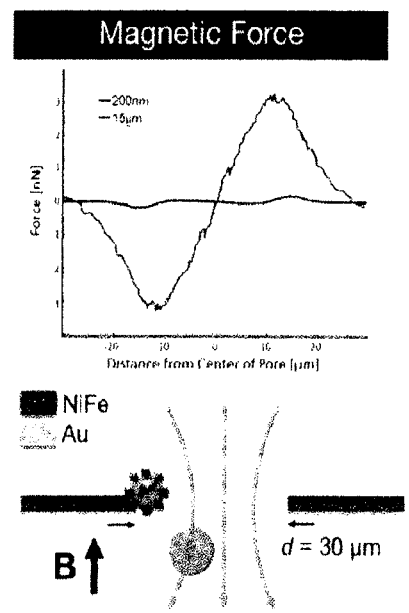
FIG. 10 shows a graph and schematic representation of the magnetic force as a function of distance from the center of the pore according to an embodiment of the present invention.
Figure 14:
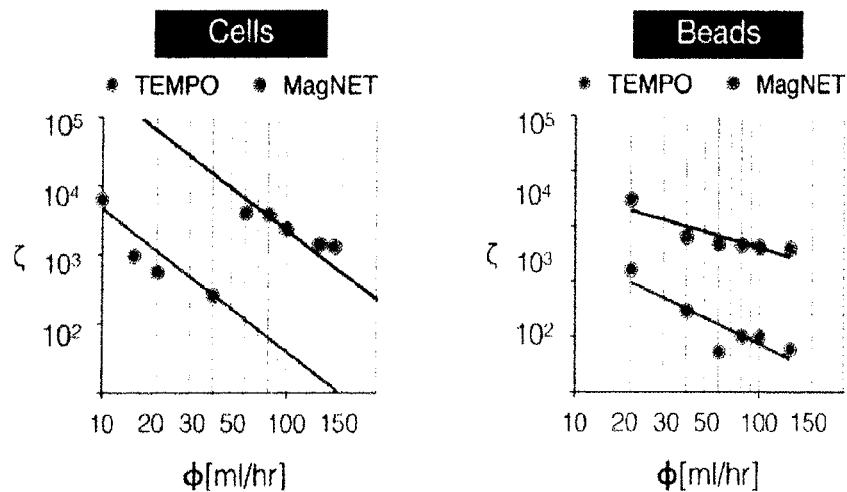
FIG. 14 shows a graph of the enrichment at a flow rate of 180 ml/h using a magnetic separation filter in accordance with the present invention.
Figure 15:
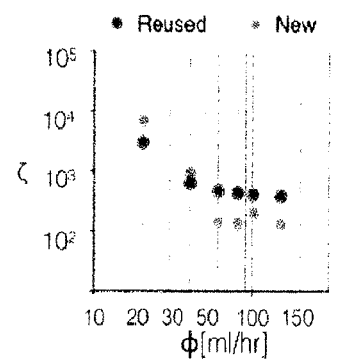
FIG. 15 shows a graph of the enrichment as a function of the flow rate of new and reused magnetic separation filters in accordance with embodiments of the present invention.

To enable high-throughput immunomagnetic sorting, a microfluidic chip with a lithography-based electroformed filter was made to capture magnetically labelled targets at high flow rates ($\Phi$=150 ml/h) and enrich pancreatic cancer cells (YFP-7591) >$10^3$ times (see FIG. 14). The filter was fabricated by electroplating permalloy ($Ni_{20}Fe_{80}$) onto a copper substrate patterned with an array of 15 µm tall, 30 µm diameter photoresist pillars (SPR220-7.0) (see FIG. 8). Once the permalloy was plated to a thickness of 15 µm, the durable film was mechanically peeled from the mold to obtain a metal filter with 30 µm pores. In the presence of an applied magnetic field, the edge of the pore creates a strong magnetic trap to capture magnetically tagged targets (see FIGS. 9 and 10). Copper molds can be replated multiple times, and filters can be reused without performance loss—offering a cost-effective fabrication strategy. Unlike conventional filter fabrication methods, lithography allows higher pore density without overlap, design of traps in any shape, and filters with area >25 $cm^2$. Vertical fluid flow through the porous filter can process 30 mL of blood in 20 min with high capture rate on a compact chip—offering a key breakthrough to enable immunomagnetic sorting to be applied for rare cell detection in clinical diagnoses. The MagNET filters were also reusable (see FIG. 15).

TEMPO vs. MagNET Filters

Figure 11:
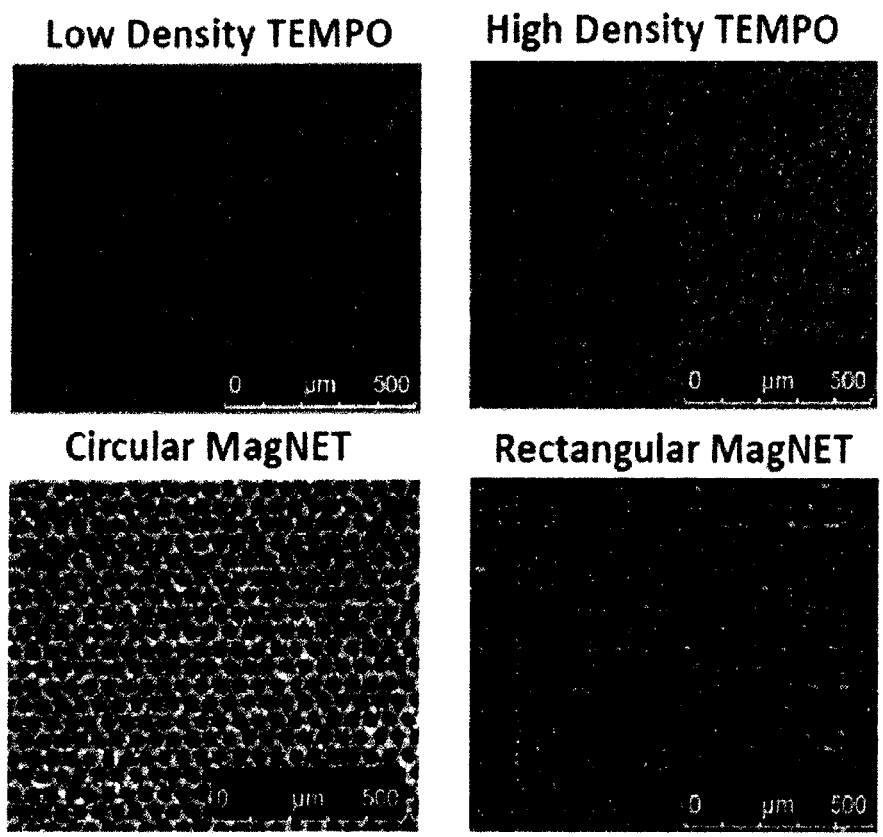
FIG. 11 shows micrographs of various magnetic separation filters in accordance with embodiments of the present invention.

A comparison of MagNET filters and TEMPO filters is shown in FIG. 11. FIG. 11 shows micrographs of a low density TEMPO filter, a high density TEMPO filter, a circular-pore MagNET filter, and a square-pore MagNET filter. As can be seen in the micrographs, the TEMPO filters have randomly distributed pores. In the high density TEMPO filter, overlap of pores may occur.

Figure 12:
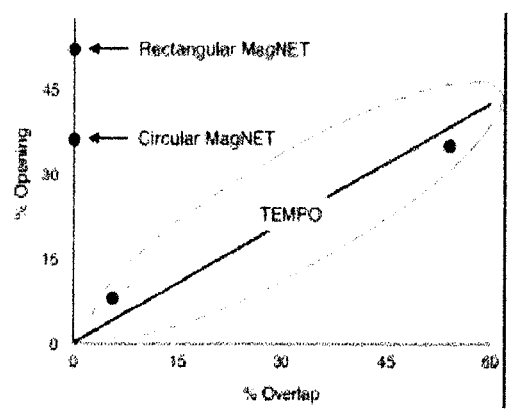
FIG. 12 shows a graph of the opening area as a function of overlap for various filters in accordance with embodiments of the present invention.
Figure 13:
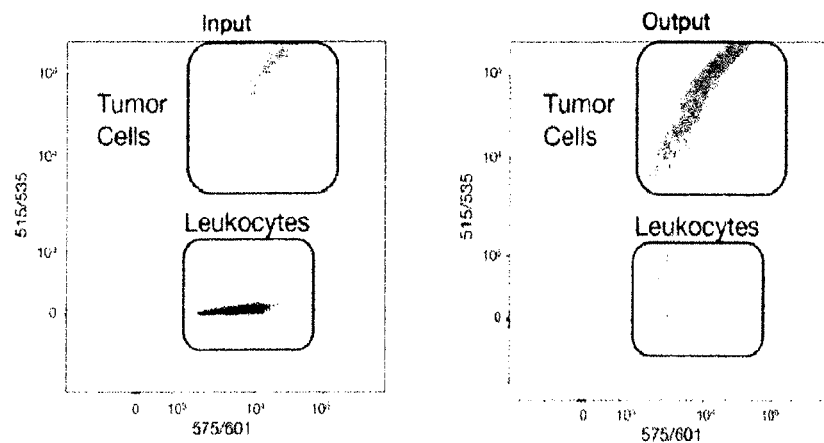
FIG. 13 shows a graph of the enrichment of filters in accordance with embodiments of the present invention as a function of flow rate.

The effective area of the pores can be increased by changing the pore shape. FIG. 12 shows a graph of the opening percentage as a function of the percentage overlap of the pores. The rectangular MagNET filter has >45% opening area with zero overlap. FIG. 13 shows a graph of the enrichment of TEMPO filters and MagNET filters made in accordance with embodiments of the present invention.

We claim:

1. A method for diagnosing a condition in a subject, comprising:
obtaining a plurality of magnetically tagged particles by magnetically labeling a fluid sample from the subject;
exposing a magnetic separation device to an external magnetic field, wherein the magnetic separation device comprises a layer of magnetically soft material comprising a plurality of pores;
flowing a suspension comprising the plurality of magnetically labeled particles through the magnetic separation device to capture the plurality of magnetically tagged particles;
removing the external magnetic field to release the plurality of magnetically labeled particles; and
detecting the presence of a biomarker that is indicative of the condition from the plurality of magnetically labeled particles.

2. The method of claim 1, wherein the layer of magnetically soft material has a thickness ranging from about 3 µm to about 50 µm.

3. The method of claim 1, wherein the pores have an average diameter ranging from about 1 µm to 200 µm.

4. The method of claim 1, wherein the magnetically soft material is a nickel-iron alloy.

5. The method of claim 1, wherein the layer of magnetically soft material comprises at least 1000 pores/$mm^2$.

6. The method of claim 1, wherein the magnetic separation device further comprises a passivation layer adjacent the layer of magnetically soft material.

7. The method of claim 6, wherein the passivation layer comprises a material chosen from nickel and gold.

8. The method of claim 1, wherein the magnetically labeled particles comprise cells, exosomes, molecules, nucleic acids, proteins, or polypeptides.

9. The method of claim 8, wherein the magnetically labeled particles comprise exosomes.

10. The method of claim 1, wherein the condition is cancer.

11. The method of claim 10, wherein the condition is pancreatic or prostate cancer.

12. The method of claim 1, wherein the condition is brain injury.

13. The method of claim 1, wherein the fluid sample is a blood sample or urine sample.

14. The method of claim 1, wherein the biomarker is a nucleic acid.

15. The method of claim 14, further comprising extracting the nucleic acid from the plurality of magnetically labeled particles.

16. The method of claim 14, wherein detecting the presence of the nucleic acid that is indicative of the condition comprises using sequencing or quantitative polymerase chain reaction (qPCR).

* * * * *